(12) United States Patent
Iwami

(10) Patent No.: US 11,195,042 B2
(45) Date of Patent: Dec. 7, 2021

(54) DRUG INSPECTION ASSISTANCE DEVICE, DRUG IDENTIFICATION DEVICE, IMAGE PROCESSING DEVICE, IMAGE PROCESSING METHOD, AND PROGRAM

(71) Applicant: FUJIFILM Toyama Chemical Co., Ltd., Tokyo (JP)

(72) Inventor: Kazuchika Iwami, Ashigarakami-gun (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/744,661

(22) Filed: Jan. 16, 2020

(65) Prior Publication Data

US 2020/0151490 A1    May 14, 2020

Related U.S. Application Data

(63) Continuation of application No. PCT/JP2018/029925, filed on Aug. 9, 2018.

(30) Foreign Application Priority Data

Aug. 22, 2017    (JP) .............................. JP2017-159559

(51) Int. Cl.
*G06K 9/44*        (2006.01)
*G06T 7/13*        (2017.01)
(Continued)

(52) U.S. Cl.
CPC ................ *G06K 9/44* (2013.01); *A61J 3/007* (2013.01); *G06K 9/4604* (2013.01); *G06T 7/13* (2017.01);
(Continued)

(58) Field of Classification Search
CPC ...... G06K 9/44; G06K 9/4604; G06K 9/2027; G06K 9/00201; G06K 9/4609;
(Continued)

(56) References Cited

U.S. PATENT DOCUMENTS

2004/0090443 A1    5/2004  Wang
2012/0290619 A1*  11/2012  DeLise, Jr. ........ G06K 9/00671
                                                      707/776
(Continued)

FOREIGN PATENT DOCUMENTS

JP    2002-334323 A    11/2002
JP     2010-4141 A      1/2010
(Continued)

OTHER PUBLICATIONS

Japanese Office Action for counterpart Japanese Application No. 2019-538069, dated Feb. 9, 2021, with English translation.
(Continued)

*Primary Examiner* — Ali Bayat
(74) *Attorney, Agent, or Firm* — Birch, Stewart, Kolasch & Birch, LLP

(57) ABSTRACT

A image processing device which can reduce information such as a pattern, a scar and the like on a surface of a drug which are other than an engraved mark, to accurately extract the engraved mark. The image processing device includes: an obtaining unit configured to obtain a plurality of images of a drug having an engraved mark on a surface of the drug, with emitting directions of light to the surface different from each other; an edge image generating unit configured to apply respectively to the plurality of images, edge extracting filters in directions in conformity with the emitting directions, the edge extracting filters having a size in conformity with a width of a groove of the engraved mark, and generate a plurality of edge images; and an image composing unit
(Continued)

configured to compose the plurality of edge images and generate a composite image.

14 Claims, 33 Drawing Sheets

(51) Int. Cl.
*G16H 70/40* (2018.01)
*A61J 3/00* (2006.01)
*G06K 9/46* (2006.01)

(52) U.S. Cl.
CPC ... *G16H 70/40* (2018.01); *G06T 2207/20221* (2013.01)

(58) Field of Classification Search
CPC ........ G16H 70/40; G16H 30/40; G16H 40/20; G16H 20/10; A61J 3/007; G06T 5/50; G06T 7/13; G06T 2207/20221; G06T 2207/10152
USPC ........................................................ 382/103
See application file for complete search history.

(56) References Cited

U.S. PATENT DOCUMENTS

| | | | |
|---|---|---|---|
| 2013/0329058 A1* | 12/2013 | Brossette | G06T 7/12 348/207.1 |
| 2014/0355849 A1* | 12/2014 | Brossette | G16H 70/40 382/128 |
| 2015/0178674 A1 | 6/2015 | Yonaha et al. | |
| 2015/0262347 A1* | 9/2015 | Duerksen | G07D 7/20 382/182 |
| 2016/0004927 A1 | 1/2016 | Yonaha | |
| 2016/0210524 A1* | 7/2016 | Hasegawa | G01N 21/85 |
| 2019/0251349 A1* | 8/2019 | Duerksen | G06T 7/0002 |
| 2019/0377977 A1* | 12/2019 | Iwami | G16H 20/13 |

FOREIGN PATENT DOCUMENTS

| | | |
|---|---|---|
| JP | 2013-88680 A | 5/2013 |
| JP | 2014-67342 A | 4/2014 |
| JP | 2014-190700 A | 10/2014 |
| JP | 2015-68765 A | 4/2015 |

OTHER PUBLICATIONS

Bukovec et al., "Automated visual inspection of imprinted pharmaceutical tablets," Measurement Science and Technology, vol. 18, 2007, pp. 2921-2930.
Extended European Search Report for counterpart European Application No. 18848786.2, dated Nov. 9, 2020.
Morimoto et al., "A Visual Inspection System for Drug Tablets," IEEE International Conference on Systems, Man, and Cybernetics (SMC), Oct. 9, 2011, pp. 1106-1110.
Yu et al., "Accurate system for automatic pill recognition using imprint information," IET Image Processing, vol. 9, Iss. 12, 2015, pp. 1039-1047.
International Preliminary Report on Patentability and Written Opinion of the International Searching Authority (Forms PCT/IB/326, PCT/IB/373 and PCT/ISA/237) for International Application No. PCT/JP2018/029925, dated Mar. 5, 2020, with English translation.
International Search Report (Form PCT/ISA/210) for International Application No. PCT/JP2018/029925, dated Nov. 6, 2018, with English translation.

* cited by examiner

DRUG INSPECTION ASSISTANCE DEVICE, DRUG IDENTIFICATION DEVICE, IMAGE PROCESSING DEVICE, IMAGE PROCESSING METHOD, AND PROGRAM

CROSS-REFERENCE TO RELATED APPLICATIONS

The present application is a Continuation of PCT International Application No. PCT/JP2018/029925 filed on Aug. 9, 2018 claiming priority under 35 U.S.C § 119(a) to Japanese Patent Application No. 2017-159559 filed on Aug. 22, 2017. Each of the above applications is hereby expressly incorporated by reference, in its entirety, into the present application.

BACKGROUND OF THE INVENTION

1. Field of the Invention

The present invention relates to a drug inspection assistance device, a drug identification device, an image processing device, an image processing method, and a program, and in particular, to a drug inspection assistance device, a drug identification device, an image processing device, an image processing method, and a program that read an engraved mark applied to a drug.

2. Description of the Related Art

There are known devices that identify a kind of a drug from a taken image obtained by imaging the drug. For example, a device illuminates a drug, takes an image of the illuminated drug, and collates a drug area of the taken image and a master image preregistered for each kind of drug, thereby identifying a kind of drug.

Japan Patent Application Laid-Open No. 2002-334323 (herein after referred to as "PTL 1") discloses an engraved mark reading device that includes: a plurality of illumination means for emitting light to an engraved mark provided on an object from different directions; imaging means for imaging the engraved mark; image composition means for composing image information obtained by the imaging means with different illuminations to obtain a composite image; and reading means for reading contents of the engraved mark from the composite image.

According to the device in PTL 1, a surface of the target object can be clarified, and the S/N (Signal to Noise) ratio of the engraved mark can be prevented from being degraded due to color irregularity and reflection irregularity.

CITATION LIST

PTL 1: Japan Patent Application Laid-Open No. 2002-334323

SUMMARY OF THE INVENTION

However, the device in PTL 1 cannot reduce the information other than that on the engraved mark. Accordingly, if the device described in PTL 1 is applied to drug identification, the device reads out a patchy pattern or the like that the drug has thereon. If information other than that on the engraved mark, such as the patchy pattern, is obtained in this manner, there is a problem that collation with the master image cannot be appropriately performed.

The present invention has been made in view of such situations, and has an object to provide a drug inspection assistance device, a drug identification device, an image processing device, an image processing method, and a program that can reduce information such as a pattern, a scar and the like on a surface of a drug which are other than an engraved mark and are smaller than a width of a groove of the engraved mark, and accurately extract the engraved mark.

To achieve the above object, an aspect of an image processing device includes: an obtaining unit configured to obtain a plurality of images of a drug having an engraved mark on a surface of the drug, with emitting directions of light to the surface different from each other; an edge image generating unit configured to apply respectively to the plurality of images, edge extracting filters in directions in conformity with the emitting directions, the edge extracting filters having a size in conformity with a width of a groove of the engraved mark, and generate a plurality of edge images; and an image composing unit configured to compose the plurality of edge images and generate a composite image.

According to this aspect, the plurality of images of the drug having the engraved mark on the surface, with emitting directions of light to the surface of the drug different from each other, are respectively subjected to the edge extracting filters in the directions in conformity with the emitting directions, the edge extracting filters having the size in conformity with the width of the groove of the engraved mark, to generate the plurality of edge images, and the plurality of edge images are composed to generate the composite image. Accordingly it is possible to reduce the information such as a pattern, a scar and the like on the surface of a drug which are other than the engraved mark and are smaller than the width of the groove of the engraved mark, and extract the engraved mark.

Preferably, the edge image generating unit applies the edge extracting filters having a larger size than half the width of the groove of the engraved mark, to generate the plurality of edge images. By using the edge extracting filter having such a size, the signal of the pattern or the like that is not dependent on the emitting directions of light relatively decreases. Accordingly, it is possible to reduce the information such as a pattern, a scar and the like on a surface of a drug which are other than that on the engraved mark and are smaller than the width of the groove of the engraved mark, and extract the engraved mark.

Preferably, the directions in conformity with the emitting directions include a direction of an emitting direction in plan view of the surface. Accordingly, the edge images can be appropriately generated.

Preferably, the directions in conformity with the emitting directions include a direction inclined by 45 degrees from the direction of the emitting direction in plan view of the surface, and a direction inclined by −45 degrees from the direction of the emitting direction in plan view of the surface. Accordingly, the edge images can be appropriately generated.

Preferably, the obtaining unit obtains four images of the drug, with the emitting directions of light to the surface being a first direction, a second direction, a third direction and a fourth direction, and the second direction is a direction opposite to the first direction in plan view of the surface, the third direction is a direction orthogonal to the first direction in plan view of the surface, and the fourth direction is a direction opposite to the third direction in plan view of the surface. By using the images on which light is emitted in four orthogonal directions, the appropriate composite image can be generated.

To achieve the above object, an aspect of a drug identification device includes: a stage configured to place a drug thereon, the drug having an engraved mark on a surface of the drug; an irradiating unit configured to include a plurality of light sources with emitting directions of light to the surface different from each other; an imaging unit configured to obtain a plurality of images taken by imaging the drug with the surface irradiated with light by the light sources; an edge image generating unit configured to apply respectively to the plurality of images, edge extracting filters in directions in conformity with the emitting directions, the edge extracting filters having a size in conformity with a width of a groove of the engraved mark, and generate a plurality of edge images; and an image composing unit configured to compose the plurality of edge images and generate a composite image.

According to this aspect, the drug having an engraved mark on its surface is placed on the stage. While the surface of the drug is irradiated with light by the light sources having emitting directions to the surface different from each other, the drug is imaged to obtain the plurality of images. The edge extracting filters that are in directions in conformity with the emitting directions and have a size in conformity with the width of the groove of the engraved mark are respectively applied to the plurality of images, to generate the plurality of edge images. The edge images are composed to generate the composite image. Accordingly, it is possible to reduce the information such as a pattern, a scar and the like on a surface of a drug which are other than that on the engraved mark and are smaller than the width of the groove of the engraved mark, and extract the engraved mark.

Preferably, the irradiating unit comprises a first light source configured to emit light in a first direction, a second light source configured to emit light in a second direction, a third light source configured to emit light in a third direction, and a fourth light source configured to emit light in a fourth direction, and the second direction is a direction opposite to the first direction in plan view of the surface, the third direction is a direction orthogonal to the first direction in plan view of the surface, and the fourth direction is a direction opposite to the third direction in plan view of the surface. The appropriate composite image can be generated by obtaining the images with light emitted in four orthogonal directions.

Preferably, the irradiating unit comprises a fifth light source configured to emit light in a fifth direction, a sixth light source configured to emit light in a sixth direction, a seventh light source configured to emit light in a seventh direction, and an eighth light source configured to emit light in an eighth direction, the sixth direction is a direction opposite to the fifth direction in plan view of the surface, the seventh direction is a direction orthogonal to the fifth direction in plan view of the surface and the eighth direction is a direction opposite to the seventh direction in plan view of the surface, the stage is made of a material having a light transparency, the first light source, the second light source, the third light source and the fourth light source are disposed on one surface side of the stage, and the fifth light source, the sixth light source, the seventh light source and the eighth light source are disposed on another surface side of the stage, the another surface side being different from the one surface side. Even if the engraved mark on the drug is disposed on any of the upper surface and the lower surface of the stage, the images are obtained with light emitted in the four orthogonal directions. Accordingly, the appropriate composite image can be generated.

To achieve the above object, an aspect of an image processing method includes: an obtaining step of obtaining a plurality of images of a drug having an engraved mark on a surface of the drug, with emitting directions of light to the surface different from each other; an edge image generating step of applying respectively to the plurality of images, edge extracting filters in directions in conformity with the emitting directions, the edge extracting filters having a size in conformity with a width of a groove of the engraved mark, to generate a plurality of edge images; and an image composing step of composing the plurality of edge images to generate a composite image.

According to this aspect, the plurality of images of the drug having the engraved mark on its surface with emitting directions of light to the surface different from each other, are respectively subjected to the edge extracting filters that are in the directions in conformity with the emitting directions and have the size in conformity with the width of the groove of the engraved mark, to generate the plurality of edge images. Then, the plurality of edge images are composed to generate the composite image. Accordingly, it is possible to reduce the information such as a pattern, a scar and the like on a surface of a drug which are other than that on the engraved mark and are smaller than the width of the groove of the engraved mark, and extract the engraved mark.

To achieve the above object, an aspect of a program causes a computer to execute: an obtaining function of obtaining a plurality of images of a drug having an engraved mark on a surface of the drug, with emitting directions of light to the surface different from each other; an edge image generating function of respectively applying the plurality of images, edge extracting filters in directions in conformity with the emitting directions, the edge extracting filters having a size in conformity with a width of a groove of the engraved mark, to generate a plurality of edge images; and an image composing function of composing the plurality of edge images to generate a composite image.

According to this aspect, the plurality of images of the drug having the engraved mark on its surface with emitting directions of light to the surface different from each other, are respectively subjected to the edge extracting filters that are in the directions in conformity with the emitting directions and have the size in conformity with the width of the groove of the engraved mark, to generate the plurality of edge images. Then, the plurality of edge images are composed to generate the composite image. Accordingly, it is possible to reduce the information such as a pattern, a scar and the like on a surface of a drug which are other than that on the engraved mark and are smaller than the width of the groove of the engraved mark, and extract the engraved mark.

To achieve the above object, an aspect of a drug inspection assistance device is a drug inspection assistance device which inspects a drug, including: a drug discriminating unit configured to collate drug master images of drugs from a drug database including drug master images, with taken images obtained by imaging drugs to be inspected, and discriminate which drugs the drugs present in the taken images are; and a list creating unit configured to create a list table of the drugs to be inspected, the list table representing drug master images of the drugs and drug area images discriminated to correspond to respective drugs in the taken images, with positions of the drug master images being aligned to positions of the drug area images, and engraved mark portions or printed character portions being enhanced.

According to this aspect, the drug master images of the drugs, and the drug area images in the taken images are displayed such that their positions are aligned to each other, and the engraved mark portions or the printed character portions are enhanced. Even if the identification information is the engraved mark or the printed character, the user can be recognize the identification information appropriately.

According to the present invention, it is possible to reduce the information such as a pattern, a scar and the like on a surface of a drug which are other than that on the engraved mark and are smaller than the width of the groove of the engraved mark, and extract the engraved mark.

DESCRIPTION OF THE PREFERRED EMBODIMENTS

Hereinafter, referring to the accompanying drawings, preferred embodiments of the present invention are described in detail.

<First Embodiment>

Identification information for identifying a kind of a drug is added to a surface of the drug (tablet). The identification information is typically added by mark engraving or character printing (print). Consequently, if it can be determined whether the identification information is added by mark engraving or by character printing, it is possible to reduce the number of candidates in a drug collation process.

Drug identification devices according to a first to third embodiments determine whether the identification information on the surface of the drug is added by mark engraving or by character printing.

Note that addition by mark engraving means that the identification information is formed by forming a groove that is a recessed area on a surface of a drug. The groove is not limited to one which has been formed by scraping the surface. Alternatively, the groove may be one which has been formed by pressing the surface. The engraved mark may include one which is not accompanied by an identification function, such as a cleavage line.

Further, addition by character printing means formation of the identification information by adding edible ink or the like through contact or noncontact on a tablet. Here, addition by character printing has the same meaning as that of addition by printing.

[Configuration of Drug Identification Device]

Figure 1:
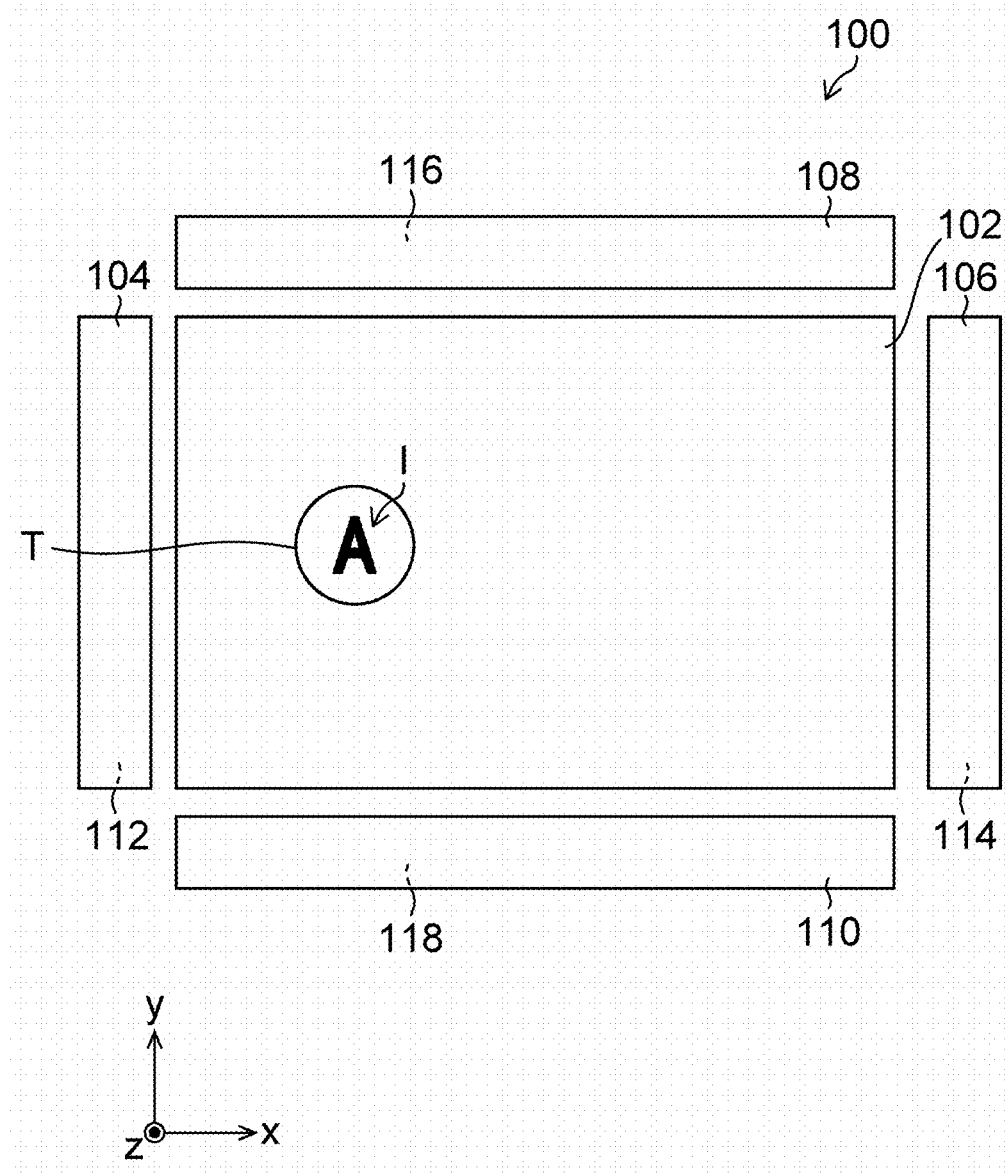
FIG. 1 is a top view of a drug identification device.
Figure 2:
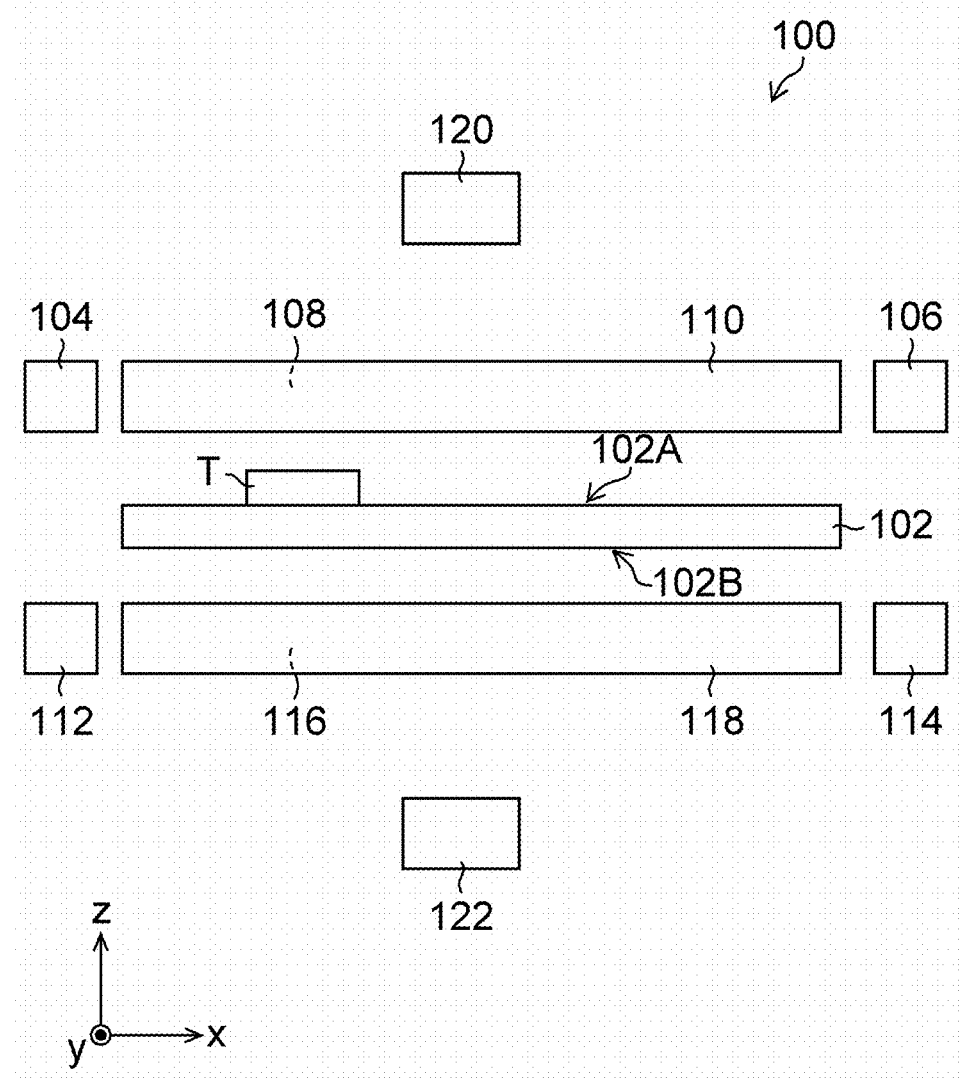
FIG. 2 is a side view of the drug identification device.

FIG. 1 is a top view of a drug identification device 100 (an example of an image processing device) according to the first embodiment. FIG. 2 is a side view of the drug identification device 100.

As shown in FIGS. 1 and 2, the drug identification device 100 includes a stage 102, a first light source 104, a second light source 106, a third light source 108, a fourth light source 110, a fifth light source 112, a sixth light source 114, a seventh light source 116, an eighth light source 118, a camera 120, and a camera 122. Note that in FIG. 1, illustration of the camera 120 and the camera 122 is omitted.

The stage 102 is a plate-shaped member that has a mounting surface 102A and a rear surface 102B, which are parallel to the xy plane (horizontal plane). The stage 102 is made of a material having light transparency. Here, the stage 102 has sizes of 130 mm in the x-axis direction, and 80 mm in the y-axis direction. A tablet T (an example of a drug) is placed on the mounting surface 102A of the stage 102. When assuming that a surface of the tablet T which is in contact with the mounting surface 102A is a lower surface and the opposite surface of the lower surface is an upper surface, identification information on the tablet T is added by mark engraving or character printing on at least one of the upper surface and the lower surface of the tablet T. Here, the tablet T is not wrapped with wrapping paper. Alternatively, the tablet T may be placed in a state of being wrapped with transparent or translucent wrapping paper.

Each of the first light source 104, the second light source 106, the third light source 108, the fourth light source 110, the fifth light source 112, the sixth light source 114, the seventh light source 116 and the eighth light source 118 is a bar-shaped (linear) LED (Light Emitting Diode) light source. The first light source 104, the second light source 106, the third light source 108, the fourth light source 110, the fifth light source 112, the sixth light source 114, the seventh light source 116 and the eighth light source 118 are supported by a supporting unit, not shown, and respectively emit illumination light that is visible light toward the stage 102 in a direction inclined from the z-axis direction. Here, the light-on luminances of the first light source 104, the second light source 106, the third light source 108, the fourth light source 110, the fifth light source 112, the sixth light source 114, the seventh light source 116 and the eighth light source 118 are equal to each other.

The first light source 104 is disposed in parallel to the y-axis direction at a position that is apart from the stage 102 by a certain amount on one side (upper side in FIG. 2) in the z-axis direction and is on one side (left side in FIG. 1) of the mounting surface 102A in the x-axis direction. The first light source 104 emits illumination light in a first direction toward the stage 102.

The second light source 106 is disposed in parallel to the y-axis direction at a position that is apart from the stage 102 by a certain amount on the one side in the z-axis direction and is on the other side (right side in FIG. 1) in the x-axis direction. The second light source 106 emits illumination light in a second direction toward the stage 102. The second direction is a direction opposite to the first direction in xy-plan view (an example of plan view of the surface).

The third light source 108 is disposed in parallel to the x-axis direction at a position that is apart from the stage 102 by a certain amount on the one side in the z-axis direction and is on one side (upper side in FIG. 1) in the y-axis direction. The third light source 108 emits illumination light in a third direction toward the stage 102. The third direction is a direction orthogonal to the first direction in the xy-plan view.

The fourth light source 110 is disposed in parallel to the x-axis direction at a position that is apart from the stage 102 by a certain amount on the one side in the z-axis direction and is on the other side (lower side in FIG. 1) in the y-axis direction. The fourth light source 110 emits illumination light in a fourth direction toward the stage 102. The fourth direction is a direction opposite to the third direction in the xy-plan view.

The fifth light source 112 is disposed in parallel to the y-axis direction at a position that is apart from the stage 102 by a certain amount on the other side (lower side in FIG. 2) in the z-axis direction and is on the one side in the x-axis direction. The fifth light source 112 emits illumination light in a fifth direction toward the stage 102. The fifth direction is the same direction as the first direction in the xy-plan view.

The sixth light source 114 is disposed in parallel to the y-axis direction at a position that is apart from the stage 102 by a certain amount on the other side in the z-axis direction and is on the other side in the x-axis direction. The sixth light source 114 emits illumination light in a sixth direction toward the stage 102. The sixth direction is a direction opposite to the fifth direction in the xy-plan view.

The seventh light source 116 is disposed in parallel to the x-axis direction at a position that is apart from the stage 102 by a certain amount on the other side in the z-axis direction and is on the one side in the y-axis direction. The seventh light source 116 emits illumination light in a seventh direction toward the stage 102. The seventh direction is a direction orthogonal to the fifth direction in the xy-plan view.

The eighth light source 118 is disposed in parallel to the x-axis direction at a position that is apart from the stage 102 by a certain amount on the other side in the z-axis direction and is on the other side in the y-axis direction. The eighth light source 118 emits illumination light in an eighth direction toward the stage 102. The eighth direction is a direction opposite to the seventh direction in the xy-plan view.

The camera 120 and the camera 122 are imaging devices that take color images of visible light, and are supported by a supporting unit, not shown. Each of the camera 120 and the camera 122 includes lenses and an imaging element.

The camera 120 is provided at a position apart from the stage 102 by a certain amount on one side of the z-axis direction. The camera 120 is disposed to face the mounting surface 102A, with the optical axis being in parallel to the z-axis direction. The camera 122 is provided at a position apart from the stage 102 by a certain amount in the other side of the z-axis direction. The camera 122 is disposed to face the rear surface 102B, with the optical axis being in parallel to the z-axis direction. The optical axis of the camera 120 and the optical axis of the camera 122 are opposite to each other via the stage 102.

Figure 3:
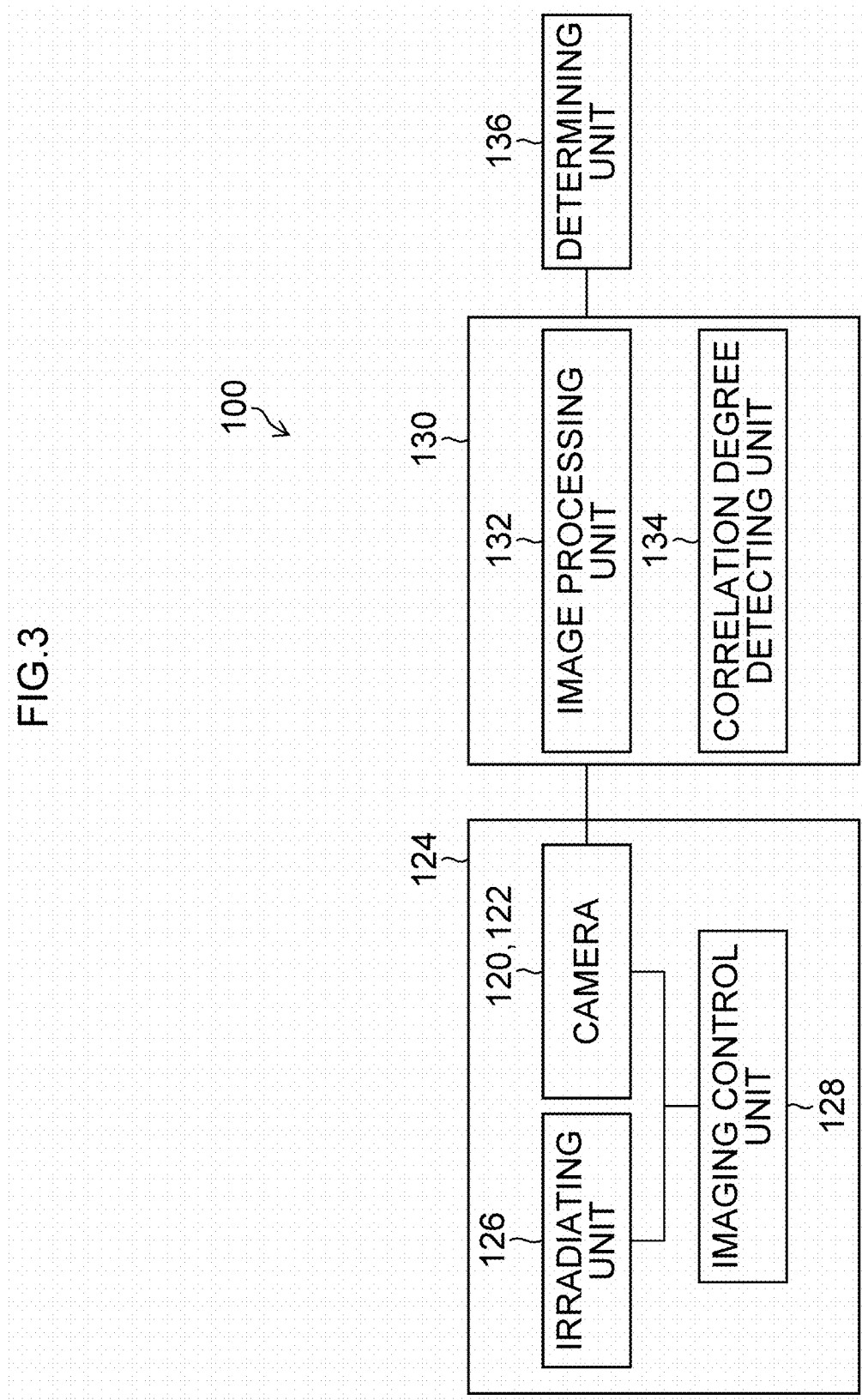
FIG. 3 is a block diagram showing an internal configuration of the drug identification device.

FIG. 3 is a block diagram showing an internal configuration of the drug identification device 100. The drug identification device 100 includes an obtaining unit 124, an image comparing unit 130, and a determining unit 136.

The obtaining unit 124 is configured to include an irradiating unit 126 and an imaging control unit 128, in addition to the camera 120 and the camera 122 described above.

The irradiating unit 126 includes multiple light sources. Here, the irradiating unit 126 includes the first light source 104, the second light source 106, the third light source 108, the fourth light source 110, the fifth light source 112, the sixth light source 114, the seventh light source 116 and the eighth light source 118, which are described above.

The imaging control unit 128 controls turning on and off of each light source of the irradiating unit 126.

The imaging control unit 128 controls the camera 120 and the camera 122. According to control by the imaging control unit 128, the camera 120 and the camera 122 each image the tablet T whose surface is irradiated with light by the multiple light sources, and obtains multiple taken images.

Note that the obtaining unit 124 may be configured to include a communication interface for communication with an external device, such as a computer, thereby obtaining from the external device, the multiple images of the tablet T where the light emitting directions onto the surface of the tablet T are different from each other.

The image comparing unit 130 compares the taken images obtained by the obtaining unit 124 with each other. The image comparing unit 130 includes an image processing unit 132 and a correlation degree detecting unit 134.

The image processing unit 132 applies image processing such as a luminance irregularity correcting process and a noise reducing process, to each of the taken images obtained by the obtaining unit 124. The correlation degree detecting unit 134 evaluates the correlation degrees between the images which have been subjected to the image processing by the image processing unit 132.

The determining unit 136 determines whether the identification information on the tablet T is added by mark engraving or by character printing according to the comparison result by the image comparing unit 130. Here, the determination is made by comparing the correlation degree detected by the correlation degree detecting unit 134 with a predetermined threshold. Note that the determining unit 136 may determine whether the engraved mark has been added on the surface of the tablet T or not.

[Image Processing Method]

An image processing method according to the first embodiment is described. Here, it is assumed that the tablet T is placed on the mounting surface 102A of the stage 102 with the identification information I being oriented on the upper side in the vertical direction. That is, the identification information I is disposed on the upper surface of the tablet T. It is preferable that there be an environment where the tablet T be not irradiated with light other than the illumination light from the light sources of the irradiating unit 126.

First, the imaging control unit 128 turns on the first light source 104, the second light source 106, the third light source 108, the fourth light source 110, the fifth light source 112, the sixth light source 114, the seventh light source 116 and the eighth light source 118, and irradiates the upper surface and the lower surface of the tablet T through the first light source 104, the second light source 106, the third light source 108, the fourth light source 110, the fifth light source 112, the sixth light source 114, the seventh light source 116 and the eighth light source 118. The imaging control unit 128 images the upper surface of the tablet T through the camera 120 and images the lower surface of the tablet T through the camera 122, and obtains an omnidirectional incident image of the upper surface and an omnidirectional incident image of the lower surface of the tablet T.

Next, the imaging control unit 128 turns on the first light source 104 and the fifth light source 112 and turns off the other light sources, and irradiates the upper surface and the lower surface of the tablet T through the first light source 104 and the fifth light source 112, respectively. The imaging control unit 128 images the upper surface of the tablet T through the camera 120 and images the lower surface of the tablet T through the camera 122, and obtains a left incident image of the upper surface and a left incident image of the lower surface of the tablet T.

Next, the imaging control unit 128 turns on the second light source 106 and the sixth light source 114 and turns off the other light sources, and irradiates the upper surface and the lower surface of the tablet T through the second light source 106 and the sixth light source 114, respectively. The imaging control unit 128 images the upper surface of the tablet T through the camera 120 and images the lower surface of the tablet T through the camera 122, and obtains a right incident image of the upper surface and a right incident image of the lower surface of the tablet T.

Subsequently, the imaging control unit 128 turns on the third light source 108 and the seventh light source 116 and turns off the other light sources, and irradiates the upper surface and the lower surface of the tablet T through the third light source 108 and the seventh light source 116, respectively. The imaging control unit 128 images the upper surface of the tablet T through the camera 120 and images the lower surface of the tablet T through the camera 122, and obtains an upper incident image of the upper surface and an upper incident image of the lower surface of the tablet T.

Furthermore, the imaging control unit 128 turns on the fourth light source 110 and the eighth light source 118 and turns off the other light sources, and irradiates the upper surface and the lower surface of the tablet T through the fourth light source 110 and the eighth light source 118, respectively. The imaging control unit 128 images the upper surface of the tablet T through the camera 120 and images the lower surface of the tablet T through the camera 122, and obtains a lower incident image of the upper surface and a lower incident image of the lower surface of the tablet T (an example of an obtaining step, and an example of an obtaining function).

The thus taken omnidirectional incident images, the left incident images, the right incident images, the upper incident images and the lower incident images are input into the image comparing unit 130.

Figure 4:
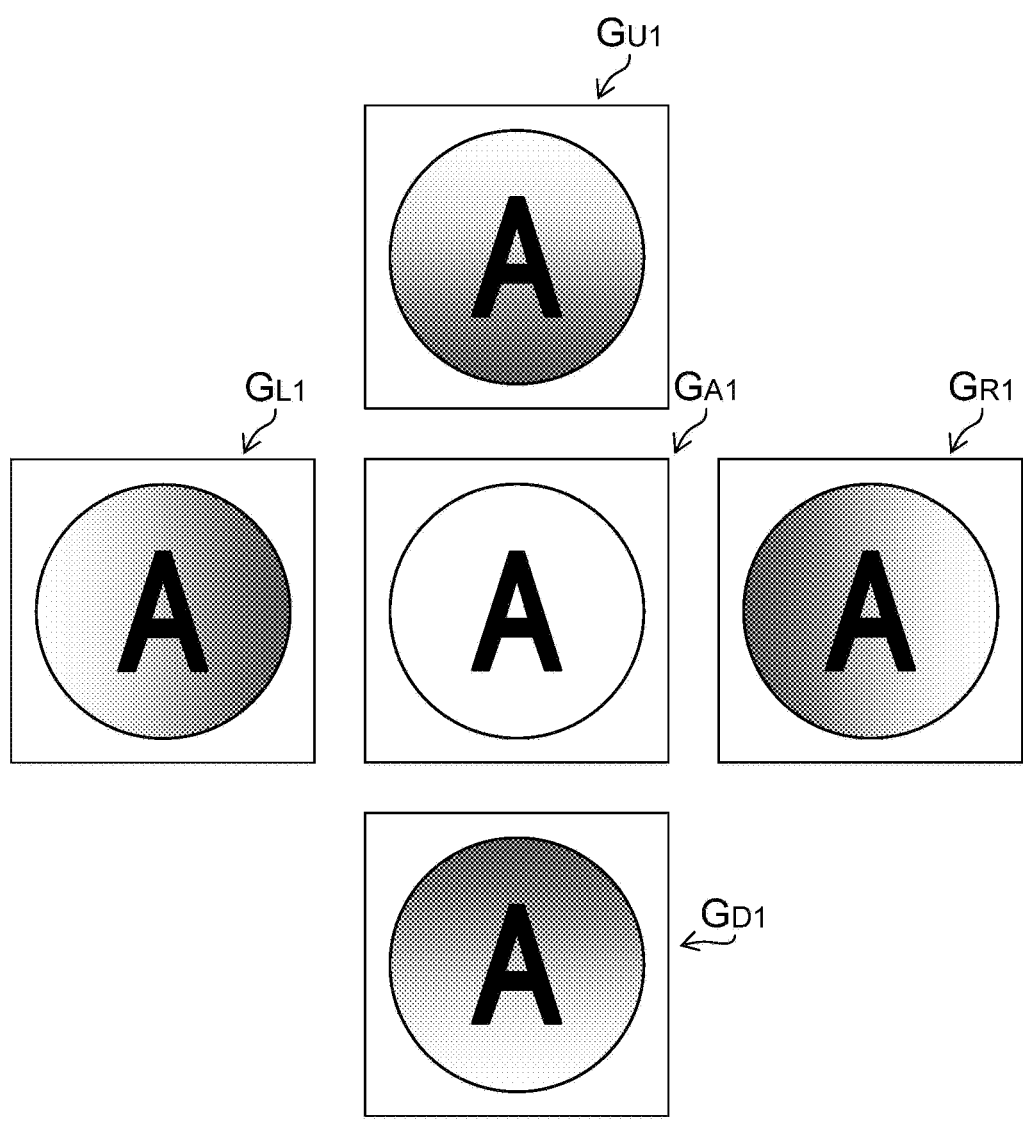
FIG. 4 shows examples of an omnidirectional incident image, a left incident image, a right incident image, an upper incident image, and a lower incident image.

The image processing unit 132 of the image comparing unit 130 extracts images in which the identification information I has been taken, from the input omnidirectional incident images, left incident images, right incident images, upper incident images and the lower incident images. Here, the identification information I is oriented on the upper side in the vertical direction. Accordingly, the identification information I has been taken by the camera 120. FIG. 4 shows the omnidirectional incident image $G_{A1}$, left incident image $G_{L1}$, right incident image $G_{R1}$, upper incident image $G_{U1}$, and lower incident image $G_{D1}$ of the upper surface of the tablet T taken by the camera 120, among the omnidirectional incident images, the left incident images, the right incident images, the upper incident images and the lower incident images obtained by the obtaining unit 124. Note that if the identification information I is oriented on the lower side in the vertical direction, the identification information I is taken by the camera 122. If multiple tablets T are placed on the stage 102 and the multiple tablets T are imaged, an area of a desired tablet T may be extracted from each image.

The image processing unit 132 applies the luminance irregularity correcting process to the omnidirectional incident image $G_{A1}$, the left incident image $G_{L1}$, the right incident image $G_{R1}$, the upper incident image $G_{U1}$ and the lower incident image $G_{D1}$, and generates an omnidirectional corrected image $G_{A2}$, a left corrected image $G_{L2}$, a right corrected image $G_{R2}$, an upper corrected image $G_{U2}$ and a lower corrected image $G_{D2}$.

The luminance irregularity correcting process is performed, for example, by dividing the omnidirectional incident image $G_{A1}$, the left incident image $G_{L1}$, the right incident image $G_{R1}$, the upper incident image $G_{U1}$ and the lower incident image $G_{D1}$, by respective images obtained by applying a Gaussian filter process to the omnidirectional incident image $G_{A1}$, the left incident image $G_{L1}$, the right incident image $G_{R1}$, the upper incident image $G_{U1}$ and the lower incident image $G_{D1}$.

Figure 5:
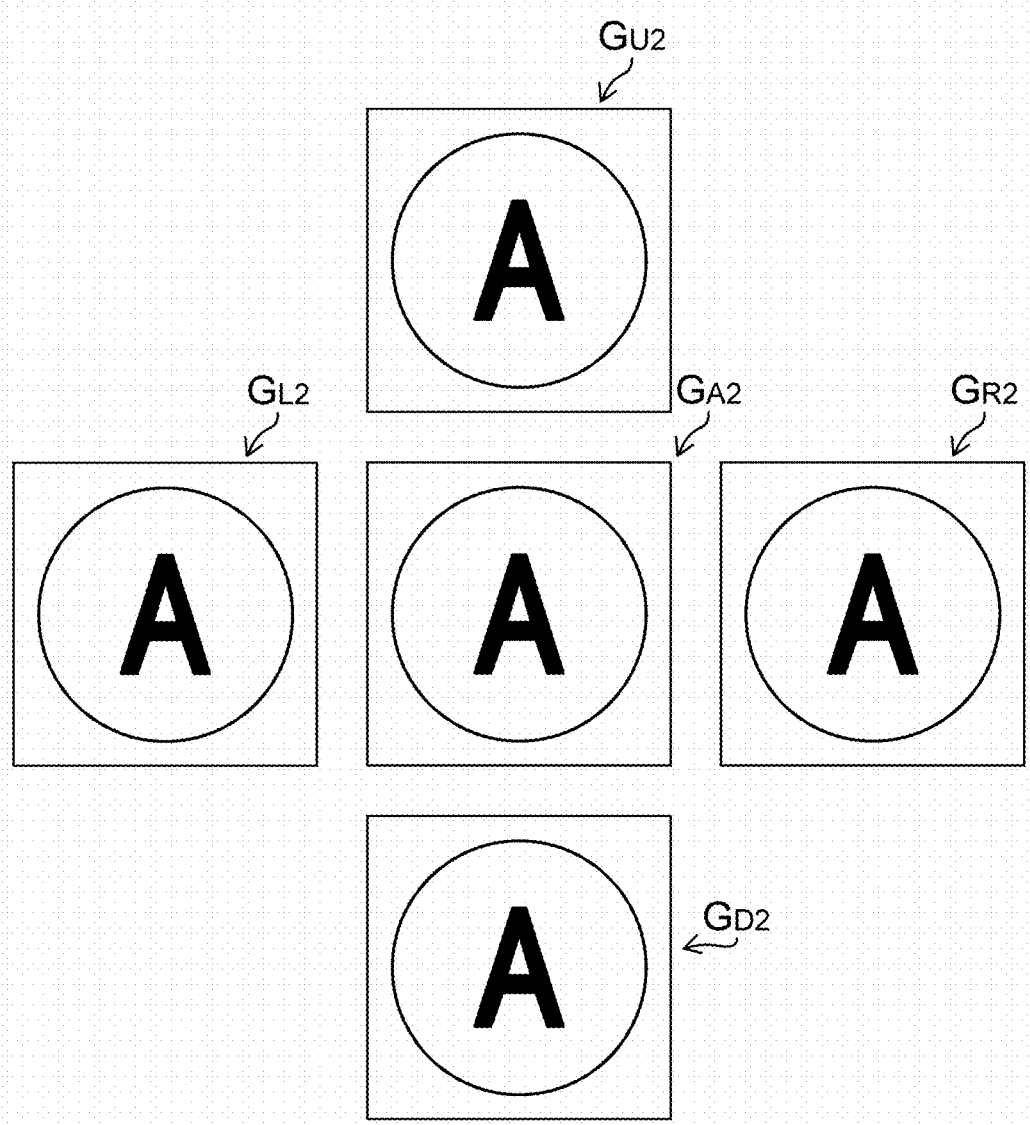
FIG. 5 shows examples of an omnidirectional corrected image, a left corrected image, a right corrected image, an upper corrected image, and a lower corrected image.

FIG. 5 shows the omnidirectional corrected image $G_{A2}$, the left corrected image $G_{L2}$, the right corrected image $G_{R2}$, the upper corrected image $G_{U2}$ and the lower corrected image $G_{D2}$ after application of the luminance irregularity correcting process in the image processing unit 132.

The image processing unit 132 may apply the noise reducing process to the omnidirectional corrected image $G_{A2}$, the left corrected image $G_{L2}$, the right corrected image $G_{R2}$, the upper corrected image $G_{U2}$ and the lower corrected image $G_{D2}$.

The noise reducing process is performed, for example, by applying a process that includes at least one of a median filter process, a Gaussian filter process, a non-local means filter process, and a Wiener filter process.

Note that the image processing unit 132 may apply the noise reducing process to the omnidirectional incident image $G_{A1}$, the left incident image $G_{L1}$, the right incident image $G_{R1}$, the upper incident image $G_{U1}$ and the lower incident image $G_{D1}$, which have not been subjected to the luminance irregularity correcting process yet.

Subsequently, the correlation degree detecting unit 134 of the image comparing unit 130 compares the omnidirectional corrected image $G_{A2}$, the left corrected image $G_{L2}$, the right corrected image $G_{R2}$, the upper corrected image $G_{U2}$ and the lower corrected image $G_{D2}$ with each other, and detects the correlation degree of the area of the identification information I (an example of the engraved mark or printed character area) in each image (an example of an image comparing step, and an example of an image comparing function). The correlation degree according to this embodiment is an index whose value increases with increase in the correlation between the compared images. The correlation degree is detected using template matching, such as zero-mean normalized cross-correlation matching, for example.

Figure 6:
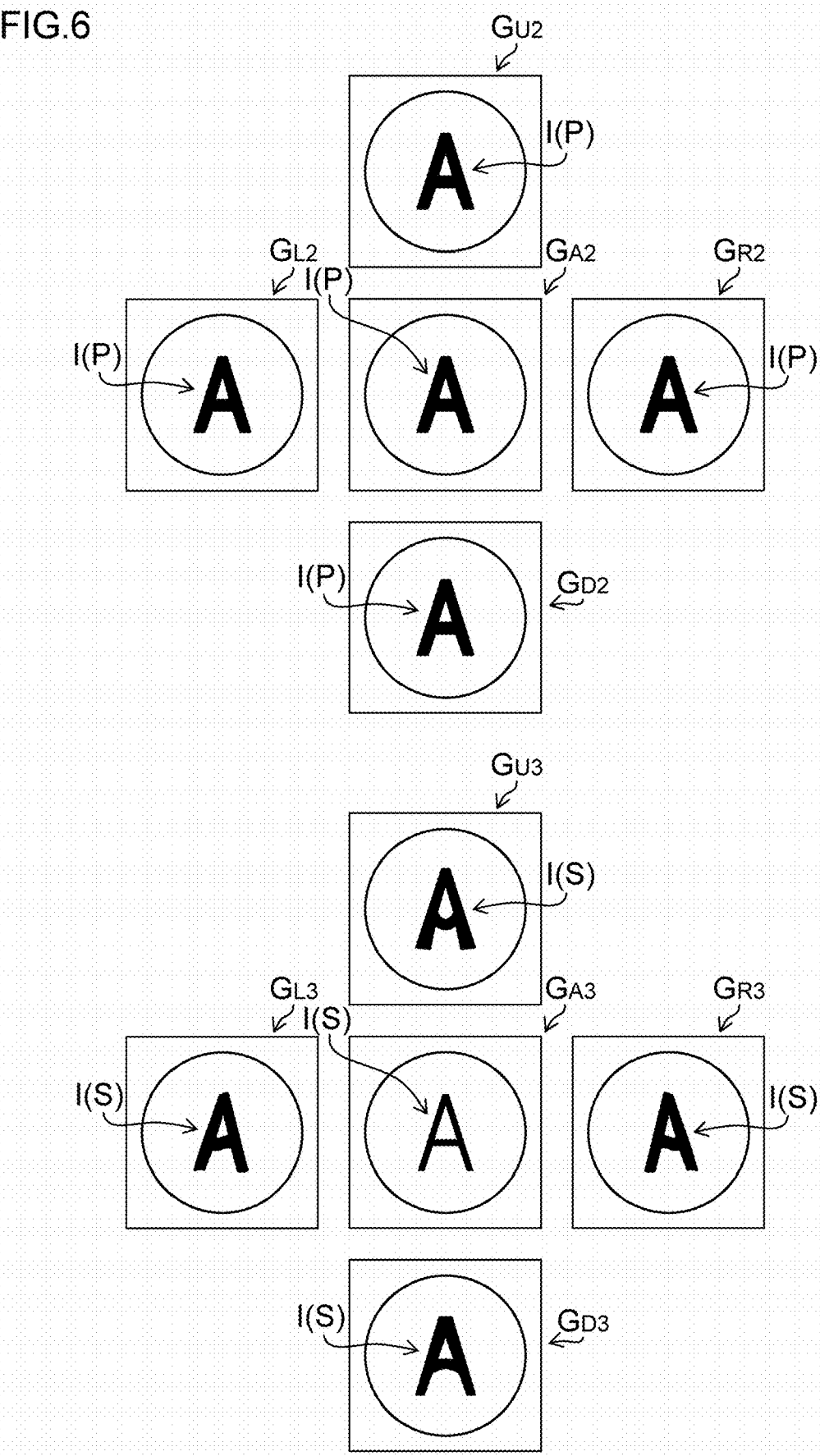
FIG. 6 shows areas of identification information on the omnidirectional corrected image, the left corrected image, the right corrected image, the upper corrected image, and the lower corrected image.

FIG. 6 shows examples of the areas of the identification information I in the omnidirectional corrected image $G_{A2}$, the left corrected image $G_{L2}$, the right corrected image $G_{R2}$, the upper corrected image $G_{U2}$ and the lower corrected image $G_{D2}$ in a case where the identification information I has been added as a printed character P, and the areas of the identification information I in an omnidirectional corrected image $G_{A3}$, a left corrected image $G_{L3}$, a right corrected image $G_{R3}$, an upper corrected image $G_{U3}$ and a lower corrected image $G_{D3}$ in a case where the identification information I has been added as an engraved mark S.

As shown in FIG. 6, in the case where the identification information I has been added as the printed character P, the contour of the identification information I is maintained (kept) without being affected by the emitting direction of the illumination light. Consequently, the correlation degree between images is relatively high. On the other hand, in the case where the identification information I has been added by the engraved mark S, the position of the shadow of the engraved mark is different depending on the emitting direction of the illumination light. Consequently, the contour of the identification information I is largely different according to the emitting direction of the illumination light. Consequently, the correlation degree between images is relatively low.

The correlation degree detected by the correlation degree detecting unit 134 is input into the determining unit 136. When the input correlation degree is higher than a predetermined threshold, the determining unit 136 determines that the identification information has been added by character printing. When the degree is equal to or less than the threshold, the determining unit 136 determines that the identification information has been added by mark engraving (an example of a determining step, and an example of a determining function).

As described above, it is possible to determine whether the identification information I is added by mark engraving or by character printing. Accordingly, the number of candidates in the collation process for the tablet T can be reduced, which can reduce the operation load and improve the speed of the collation process.

In this embodiment, by emitting the illumination light in the four directions, four incident images in the respective directions and one omnidirectional incident image are obtained. Alternatively, by emitting illumination light in two directions, two incident images in the respective directions and one omnidirectional incident image may be obtained. Note that it is preferable to emit illumination light in three or more directions so as to obtain three or more incident images in respective directions and one omnidirectional incident image.

<Second Embodiment>
[Configuration of Drug Identification Device]

Figure 7:
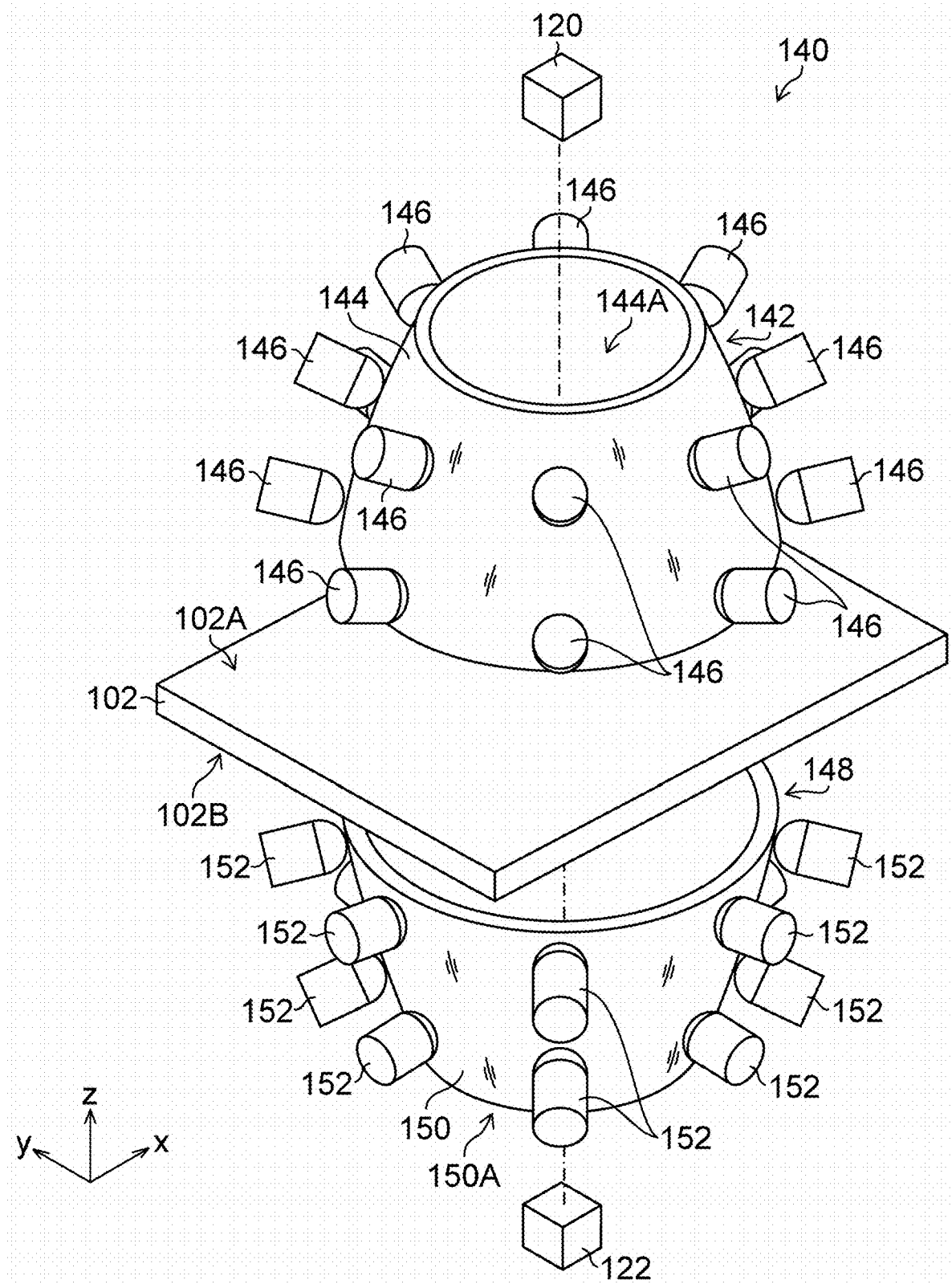
FIG. 7 is a perspective view of the drug identification device.
Figure 8:
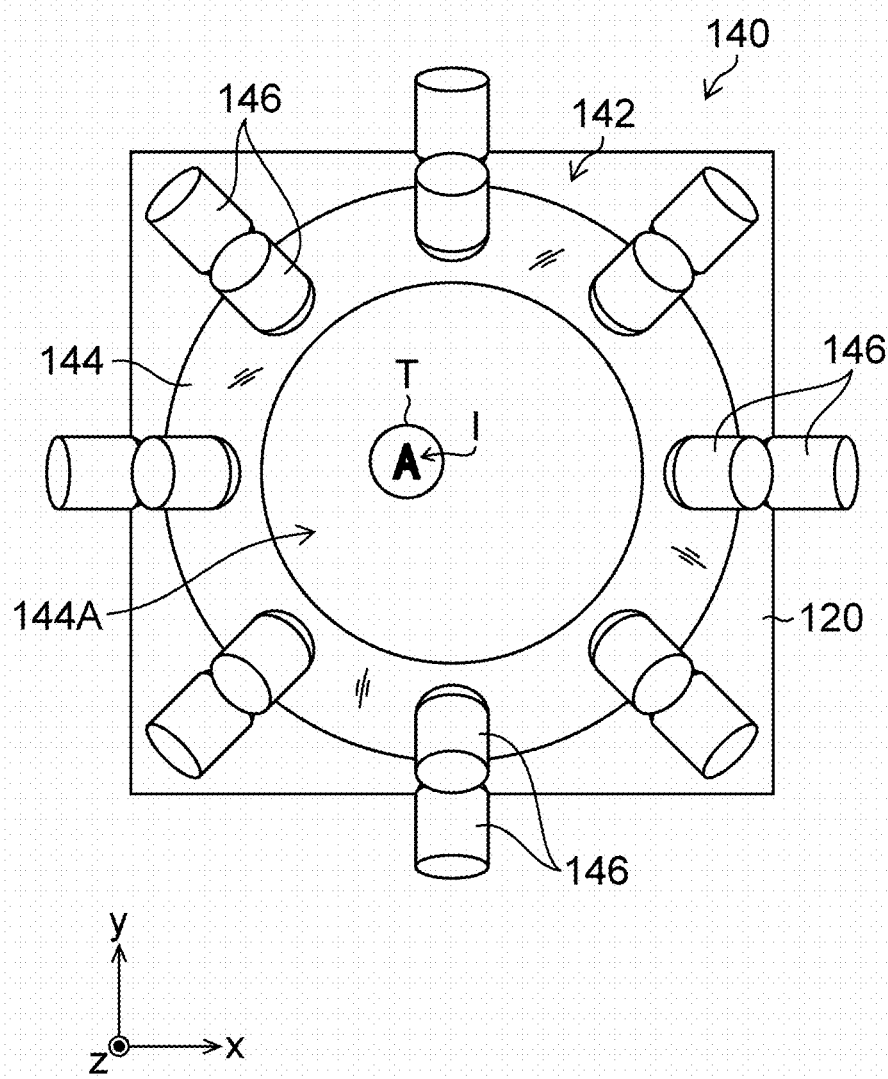
FIG. 8 is a top view of a drug identification device.

FIG. 7 is a perspective view of a drug identification device 140 according to a second embodiment. FIG. 8 is a top view of the drug identification device 140. Note that the parts common to those of the drug identification device 100 shown in FIGS. 1 and 2 are assigned the same numerals or characters; their detailed description is omitted.

As shown in FIGS. 7 and 8, the drug identification device 140 includes a stage 102, a camera 120, a camera 122, a mounting-surface-side dome lamp 142, and a rear-surface-side dome lamp 148. Note that in FIG. 8, illustration of the camera 120, the camera 122 and the rear-surface-side dome lamp 148 is omitted.

The mounting-surface-side dome lamp 142 is supported by a supporting unit, not shown, at a position apart by a certain amount from the stage 102 on one side (on a mounting surface 102A side) in the z-axis direction. The mounting-surface-side dome lamp 142 is configured to include a light source supporting unit 144 and a plurality of point light sources 146. The light source supporting unit 144 is a supporting member that supports the point light sources 146. The light source supporting unit 144 is formed of a material having light transparency. The light source supporting unit 144 is formed to be substantially dome-shaped.

An opening window 144A is formed on the upper side of the light source supporting unit 144 in the vertical direction. The inside of the light source supporting unit 144 is exposed through the opening window 114A. The camera 120 is disposed above the opening window 144A in the vertical direction. Accordingly, via the opening window 144A, the tablet T in the light source supporting unit 144 can be imaged by the camera 120. The tablet T in the light source supporting unit 144 means a tablet T that is placed on the stage 102 and disposed inside of the light source supporting unit 144.

An LED light source is used for each point light source 146. Eight point light sources 146 are attached to each of the lower part and the upper part of the outer surface of the light source supporting unit 144 at regular intervals along the respective circumferential directions. The sixteen point light sources 146 each emit illumination light toward the tablet T inside of the light source supporting unit 144.

The rear-surface-side dome lamp 148 is supported by a supporting unit, not shown, at a position apart by a certain amount from the stage 102 on the other side (on a rear surface 102B side) in the z-axis direction. The rear-surface-side dome lamp 148 is configured to include a light source supporting unit 150, and a plurality of point light sources 152. The light source supporting unit 150 is configured in a similar manner to the light source supporting unit 144 of the mounting-surface-side dome lamp 142.

An opening window 150A is formed on the lower side of the light source supporting unit 150 in the vertical direction. The inside of the light source supporting unit 150 is exposed through the opening window 150A. The camera 122 is disposed below the opening window 150A in the vertical direction. Accordingly, via the opening window 150A, the tablet T in the light source supporting unit 150 can be imaged by the camera 122. The tablet T in the light source supporting unit 150 means a tablet T that is placed on the stage 102 and disposed inside of the light source supporting unit 150.

The configuration and arrangement of the point light sources 152 are similar to those of the point light sources 146 of the mounting-surface-side dome lamp 142. Here, the light-on luminances of the point light sources 146 and the point light sources 152 are equal to each other.

The block diagram showing the internal configuration of the drug identification device 140 is analogous to the block diagram of the drug identification device 100 shown in FIG. 3. The point light sources 146 and the point light sources 152 are included in the irradiating unit 126.

The thus configured drug identification device 140 can irradiate the tablet T in the light source supporting unit 144 with illumination light in arbitrary emitting directions, by controlling turning on and off each of the point light sources 146 of the mounting-surface-side dome lamp 142 and the point light sources 152 of the rear-surface-side dome lamp 148.

[Image Processing Method]

An image processing method according to the second embodiment is described. As with the first embodiment, it is assumed that the tablet T is placed on the mounting surface 102A of the stage 102, with the identification information I being oriented on the upper side in the vertical direction.

First, the imaging control unit 128 of the drug identification device 140 turns on all of the point light sources 146 of the mounting-surface-side dome lamp 142 and the point light sources 152 of the rear-surface-side dome lamp 148. Accordingly, the point light sources 146 irradiate the surface (upper surface) of the tablet T with light in multiple (here, sixteen) directions inclined from the vertical direction. The point light sources 152 irradiate the surface (lower surface) of the tablet T with light in multiple (here, sixteen) directions inclined from the vertical direction.

The imaging control unit 128 images the upper surface of the tablet T through the camera 120 and images the lower surface of the tablet T through the camera 122, and obtains an omnidirectional incident image of the upper surface of the tablet T and an omnidirectional incident image of the lower surface.

Next, the imaging control unit 128 turns on one point light source 146 among the point light sources 146 of the mounting-surface-side dome lamp 142, and turns off the remaining lamps. Likewise, this unit turns on one point light source 152 among the point light sources 152 of the rear-surface-side dome lamp 148, and turns off the remaining lamps. As described above, the point light sources 146 and the point light sources 152 each emit light in one direction inclined from the direction perpendicular to the surface of the tablet T.

The imaging control unit 128 then images the tablet T through the camera 120 and the camera 122, and obtains a unidirectional incident image of the upper surface of the tablet T and a unidirectional incident image of the lower surface. The omnidirectional incident images and the unidirectional incident images are input into the image comparing unit 130.

From the input omnidirectional incident images and unidirectional incident images, the image processing unit 132 of the image comparing unit 130 extracts images in which the identification information I has been taken, that is, the omnidirectional incident image and unidirectional incident images that have been imaged by the camera 120. The image processing unit 132 applies the luminance irregularity correcting process to the extracted omnidirectional incident image and unidirectional incident images, and generates omnidirectional corrected image and unidirectional corrected images.

Subsequently, the correlation degree detecting unit 134 of the image comparing unit 130 compares the omnidirectional corrected image and the unidirectional corrected images, and detects the correlation degree of the area of the identification information I for each image.

In the case where the identification information I is added by mark engraving, the signal of the area of the identification information I in the unidirectional corrected image (unidirectional incident image) is resistant to attenuation, but the signal of the area of the identification information I in the omnidirectional corrected image (omnidirectional incident image) is attenuated by diffusion. Accordingly, the correlation degree between the area of the identification information I in the omnidirectional corrected image (omnidirectional incident image) and the area of the identification information I in the unidirectional corrected image (unidirectional incident image) becomes relatively low.

On the other hand, in the case where the identification information I is added by character printing, both the signals of the area of the identification information I in the omnidirectional corrected image (omnidirectional incident image) and the area of the identification information I in the unidirectional corrected image (unidirectional incident image) are resistant to attenuation. Accordingly, the correlation degree between the area of the identification information I in the omnidirectional corrected image (omnidirectional incident image) and the area of the identification information I in the unidirectional corrected image (unidirectional incident image) becomes relatively high.

The correlation degree detected by the correlation degree detecting unit 134 is input into the determining unit 136. When the input correlation degree is higher than a predetermined threshold, the determining unit 136 determines that the identification information has been added by character printing. When the degree is equal to or less than the threshold, the determining unit 136 determines that the identification information has been added by mark engraving.

As described above, it can be determined whether the identification information I has been added by mark engraving or by character printing. Accordingly, the number of candidates in the collation process for the tablet T can be reduced, which can reduce the operation load and improve the speed of the collation process.

Note that the drug identification device 140 may control turning on and off of each of the point light sources 146 of the mounting-surface-side dome lamp 142 and the point light sources 152 of the rear-surface-side dome lamp 148 so as to obtain omnidirectional (four-directional) incident images, left incident images, right incident images, upper incident images, and lower incident images, which are analogous to those of the first embodiment.

<Third Embodiment>

[Configuration of Drug Identification Device]

Figure 9:
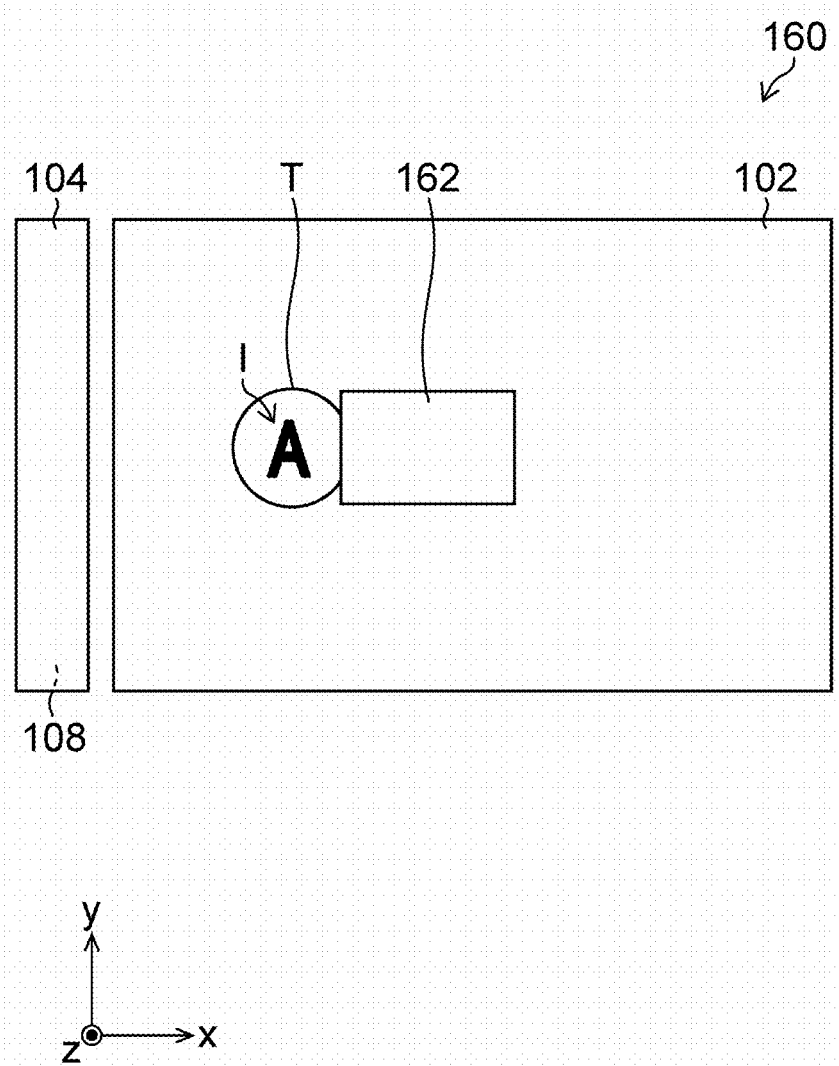
FIG. 9 is a top view of a drug identification device.
Figure 10:
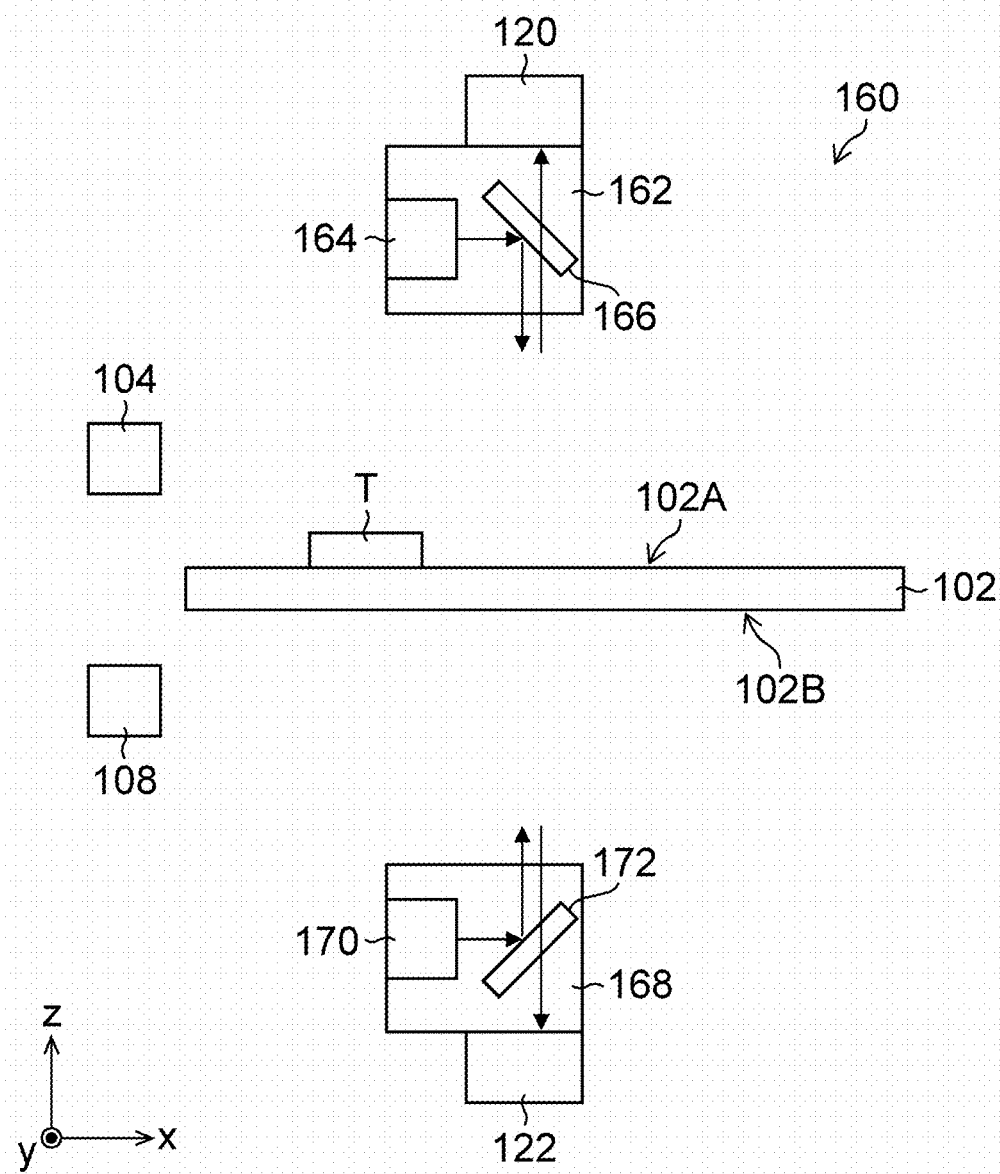
FIG. 10 is a side view of the drug identification device.

FIG. 9 is a top view of a drug identification device 160 according to a third embodiment. FIG. 10 is a side view of the drug identification device 160. Note that the parts common to those of the drug identification device 100 shown in FIGS. 1 and 2 are assigned the same numerals or characters, and their detailed description is omitted.

As shown in FIGS. 9 and 10, the drug identification device 160 includes a stage 102, a first light source 104, a fifth light source 112, a camera 120, a camera 122, a first epi-illumination lamp 162, and a second epi-illumination lamp 168. Note that in FIG. 9, illustration of the camera 120, the camera 122 and the second epi-illumination lamp 168 is omitted.

The first epi-illumination lamp 162 is disposed on the optical axis of the camera 120 between the stage 102 and the camera 120 and is supported by a supporting unit, not shown. The first epi-illumination lamp 162 includes a light source 164 and a half mirror 166.

An LED light source is used for the light source 164. The half mirror 166 reflects illumination light emitted from the light source 164, to the direction coinciding with the optical axis of the camera 120. The half mirror 166 transmits reflected light coming back from the stage 102, and allows the light to enter the camera 120. As described above, the first epi-illumination lamp 162 emits epi-illumination light coaxial with the optical axis of the camera 120, toward the mounting surface 102A of the stage 102.

The second epi-illumination lamp 168 is supported by a supporting unit, not shown, on the optical axis of the camera 122 between the stage 102 and the camera 122. The second epi-illumination lamp 168 includes a light source 170 and a half mirror 172.

An LED light source is adopted as the light source 170. The half mirror 172 reflects illumination light emitted from the light source 170, to the direction coinciding with the optical axis of the camera 122. The half mirror 172 transmits reflected light coming back from the stage 102, and allows the light to enter the camera 122. As described above, the second epi-illumination lamp 168 emits epi-illumination light coaxial with the optical axis of the camera 122, toward the rear surface 102B of the stage 102.

The block diagram showing the internal configuration of the drug identification device 160 is analogous to the block diagram of the drug identification device 100 shown in FIG. 3. In the diagram, the light source 164 and the light source 170 are included in the irradiating unit 126.

In the thus configured drug identification device 160, the surface of the tablet T can be irradiated with the illumination light in an inclined direction by each of the first light source 104 and the fifth light source 112. In addition, the surface of the tablet T can be irradiated with the illumination light in the epi-illumination direction (vertical direction) by each of the first epi-illumination lamp 162 and the second epi-illumination lamp 168.

[Image Processing Method]

An image processing method according to the third embodiment is described. As with the first embodiment, it is assumed that the tablet T is placed on the mounting surface 102A of the stage 102, with the identification information I being oriented on the upper side in the vertical direction.

First, the imaging control unit 128 of the drug identification device 160 turns on the first light source 104 and the fifth light source 112, and turns off the first epi-illumination lamp 162 and the second epi-illumination lamp 168. The imaging control unit 128 images the upper surface of the tablet T with the camera 120 and images the lower surface of the tablet T with the camera 122, and obtains a unidirectional incident image of the upper surface of the tablet T and a unidirectional incident image of the lower surface.

Next, the imaging control unit 128 turns on the first epi-illumination lamp 162 and the second epi-illumination lamp 168, and turns off the first light source 104 and the fifth light source 112. This unit then images the upper surface of the tablet T through the camera 120 and images the lower surface of the tablet T through the camera 122, and obtains an epi-illumination image of the upper surface of the tablet T and an epi-illumination image of the lower surface. The unidirectional incident images and epi-illumination images are input into the image comparing unit 130.

From the input unidirectional incident images and epi-illumination images, the image processing unit 132 of the image comparing unit 130 extracts images in which the identification information I has been taken, that is, the unidirectional incident image and epi-illumination image which have been imaged by the camera 120. The image processing unit 132 applies the luminance irregularity correcting process to the extracted unidirectional incident image and epi-illumination image, and generates a unidirectional corrected image and an epi-illumination corrected image.

Subsequently, the correlation degree detecting unit 134 of the image comparing unit 130 compares the unidirectional corrected image and the epi-illumination corrected image, and detects the correlation degree of the area of the identification information I in each image.

In the case where the identification information I is added by mark engraving, the signal of the area of the identification information I in the unidirectional corrected image (unidirectional incident image) is resistant to attenuation, but the signal of the area of the identification information I in the epi-illumination corrected image (epi-illumination image) is attenuated by diffusion. Accordingly, the correlation degree between the area of the identification information I in the epi-illumination corrected image (epi-illumination image) and the area of the identification information I in the unidirectional corrected image (unidirectional incident image) becomes relatively low.

On the other hand, in the case where the identification information I is added by character printing, both the signals of the area of the identification information I in the epi-illumination corrected image (epi-illumination image) and the area of the identification information I in the unidirectional corrected image (unidirectional incident image) are resistant to attenuation. Accordingly, the correlation degree between the area of the identification information I in the epi-illumination corrected image (epi-illumination image) and the area of the identification information I in the unidirectional corrected image (unidirectional incident image) becomes relatively high.

The correlation degree detected by the correlation degree detecting unit 134 is input into the determining unit 136. When the input correlation degree is higher than a predetermined threshold, the determining unit 136 determines that the identification information has been added by character printing. When the degree is equal to or less than the threshold, the determining unit 136 determines that the identification information has been added by mark engraving.

As described above, it can be determined whether the identification information I has been added by mark engraving or by character printing. Accordingly, the number of candidates in the collation process for the tablet T can be reduced, which can reduce the load in the operation process of collation.

<Fourth Embodiment>

If the engraved mark and the cleavage line of the tablet are extracted, the robustness of collation of the tablet is improved. The same applies to a case of comparison between images such as the local feature amount or template matching, in collation, and a case of character recognition such as OCR (Optical Character Recognition).

The reason why robustness is reduced is that images to be compared are different from each other in all cases. In particular, in a case where the positional relationship between the light source and the engraved mark and cleavage line is haphazardly determined, the difference in the engraved mark and cleavage line between images becomes significant. This is because the situation of occurrence of the shadow varies depending on the positional relationship between the light source and the engraved mark and cleavage line.

The drug identification devices according to the fourth to fifth embodiments use the relationship between the light emitting direction and the direction in which the shadow of the engraved mark occurs, to perform an edge extracting filter process in conformity with the light emitting direction and extract only a groove portion of the tablet. Accordingly, even in a case where the positional relationship between the light source and the engraved mark is haphazardly determined, it is possible to reduce information such as a pattern, a scar and the like on a surface of a drug, which are information other than an engraved mark and smaller than a width of a groove of the engraved mark, and accurately extract the engraved mark.

[Configuration of Drug Identification Device]

Figure 11:
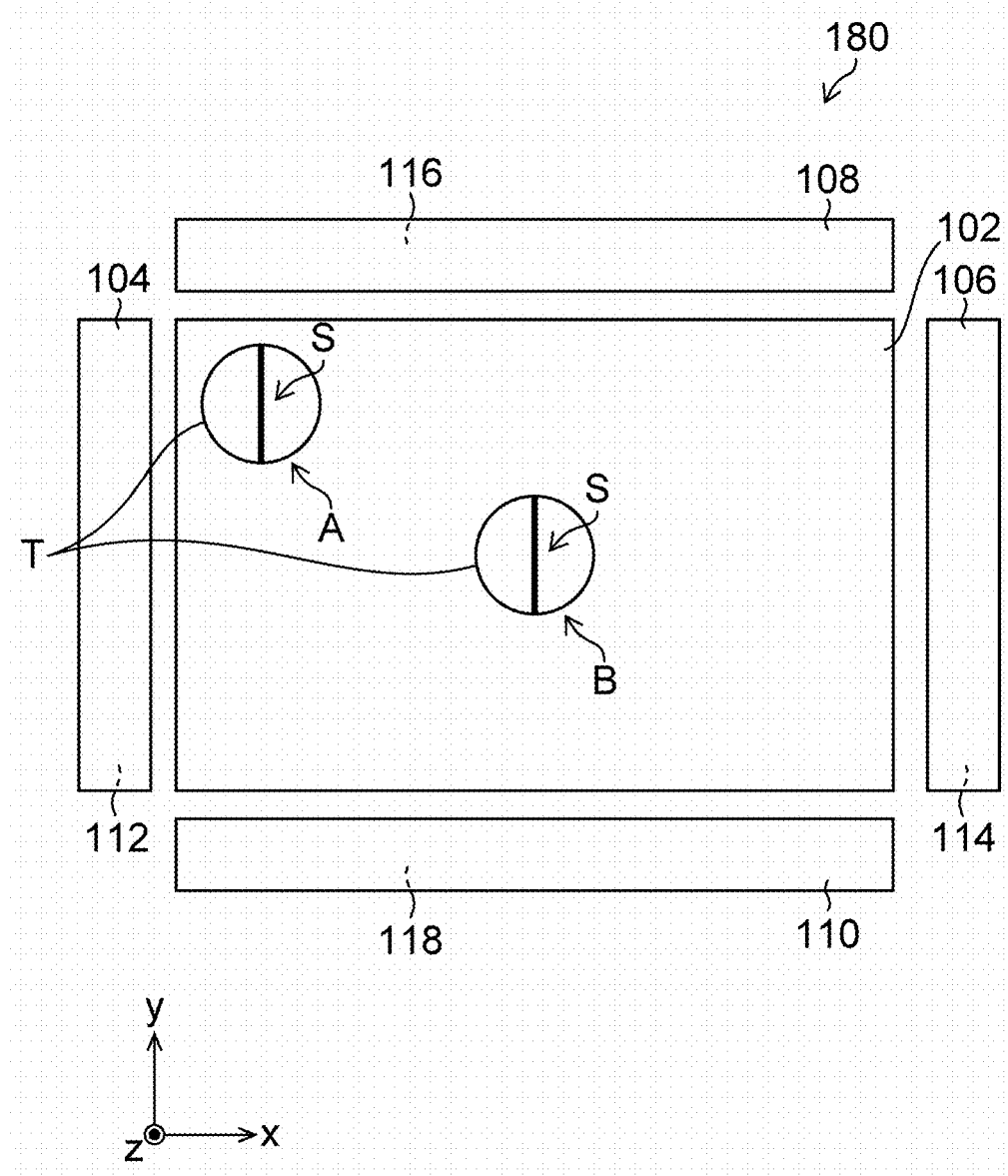
FIG. 11 is a top view of a drug identification device.
Figure 12:
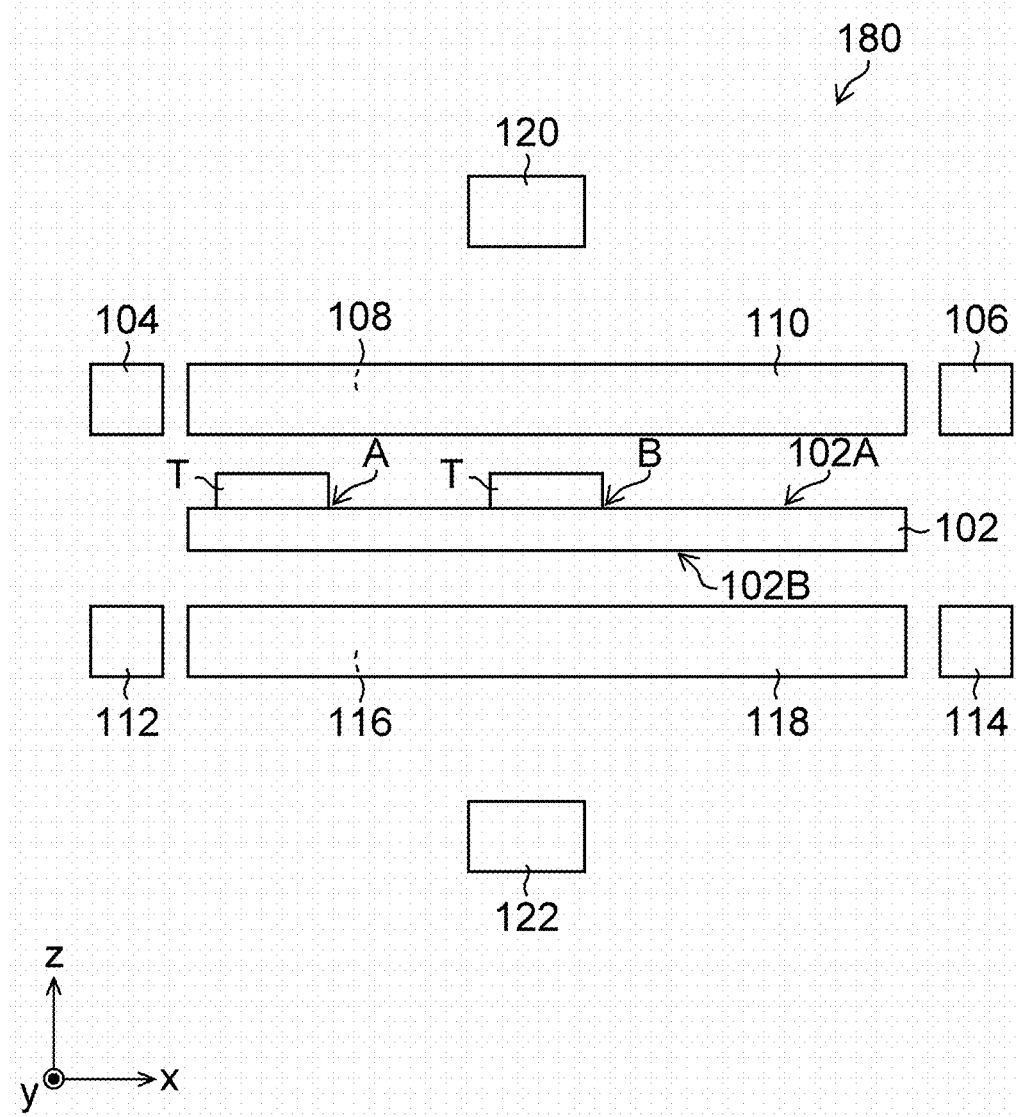
FIG. 12 is a side view of the drug identification device.

FIG. 11 is a top view of a drug identification device 180 according to a fourth embodiment. FIG. 12 is a side view of the drug identification device 180. The configuration of the drug identification device 180 in external appearance is common to the configuration of the drug identification device 100 shown in FIGS. 1 and 2. The drug identification device 180 includes a stage 102, a first light source 104, a second light source 106, a third light source 108, a fourth light source 110, a fifth light source 112, a sixth light source 114, a seventh light source 116, an eighth light source 118, a camera 120, and a camera 122. Here, an example where a tablet T is placed at each of a position A and a position B is shown.

The tablets T each have a diameter of D. An engraved mark S that is a cleavage line which is a groove having a V-shaped cross-section is formed on a surface of each of the tablets T. The width of the groove of the engraved mark S is W. Note that the width of the groove of the engraved mark S means a distance from one end of the groove to the other end in a direction orthogonal to the groove extending direction, on the surface of the tablet T. In the example shown in FIG. 11, the tablets T are placed on the stage 102, with the engraved marks S being oriented on the upper side in the vertical direction and with the engraved marks S being in parallel to the y-axis direction.

Figure 13:
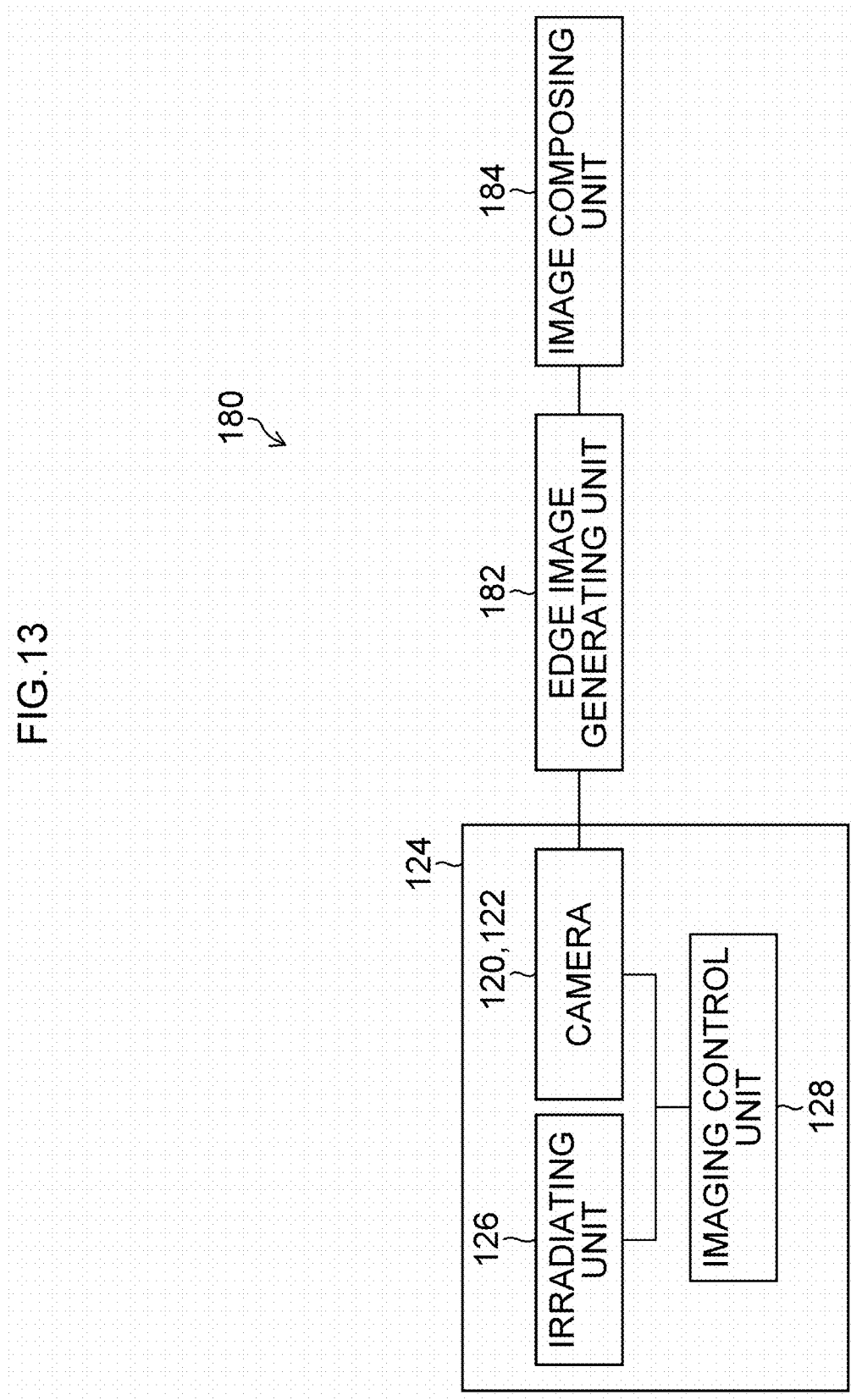
FIG. 13 is a block diagram showing an internal configuration of the drug identification device.

FIG. 13 is a block diagram showing the internal configuration of the drug identification device 180. Note that the parts common to the block diagram shown in FIG. 3 are assigned the same numerals or characters; and their detailed description is omitted. The drug identification device 180 includes an obtaining unit 124, an edge image generating unit 182 and an image composing unit 184.

The obtaining unit 124 obtains a plurality of images of each drug having an engraved mark thereon. In the plurality images, the light emitting directions onto the surface of the drug are different from each other. In this embodiment, images having a resolution of 360 dpi (dot per inch) are obtained by the camera 120 and the camera 122.

The edge image generating unit 182 applies an edge extracting filter that is in a direction in conformity with the emitting direction of the illumination light and has a size in conformity with the width of the groove of the engraved mark to each of the images obtained by the obtaining unit 124, and generates a plurality of edge images.

The image composing unit 184 composes the edge images generated by the edge image generating unit 182 and generates a composite image.

[Difference in Shadow Occurrence According to Positional Relationship Between Light Source and Engraved Mark]

Here, the difference in shadow occurrence according to the positional relationship between the light source and the engraved mark (cleavage line) is described.

Figure 14:
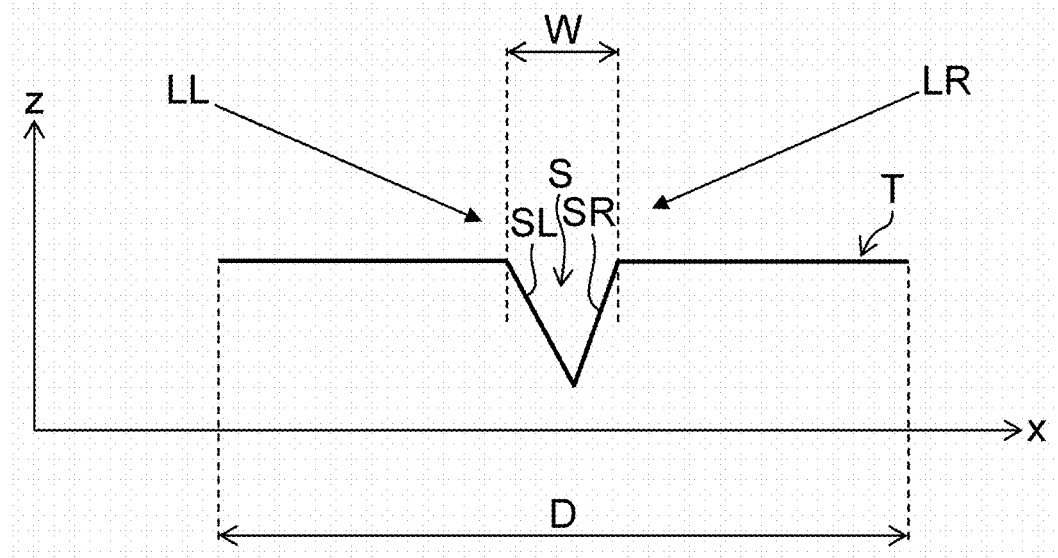
FIG. 14 is a schematic diagram of sectional structure taken along the x-axis direction passing through the center of a tablet in the xy-plan view.

FIG. 14 is a schematic diagram of the sectional structure of the tablet T shown in FIG. 11, along the x-axis direction passing through the center of the tablet T in the xy-plan view. FIG. 14 indicates a profile of a line for one pixel.

Here, the imaging control unit 128 turns on only the first light source 104 among the light sources of the irradiating unit 126, and emits illumination light $L_L$ shown in FIG. 14 from the first light source 104 to the tablet T placed on the stage 102. The upper surface of the tablet T is then imaged by the camera 120, and the left incident image is obtained.

Figure 15:
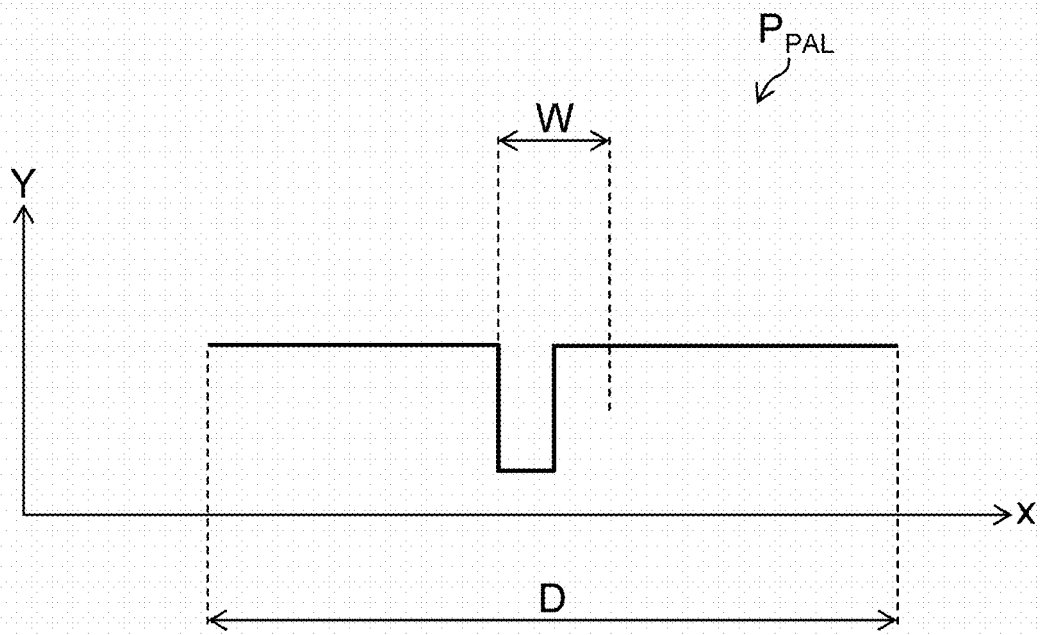
FIG. 15 shows a luminance profile taken along the x-axis direction passing through the center of a left incident image of the tablet in the xy-plan view.
Figure 15:
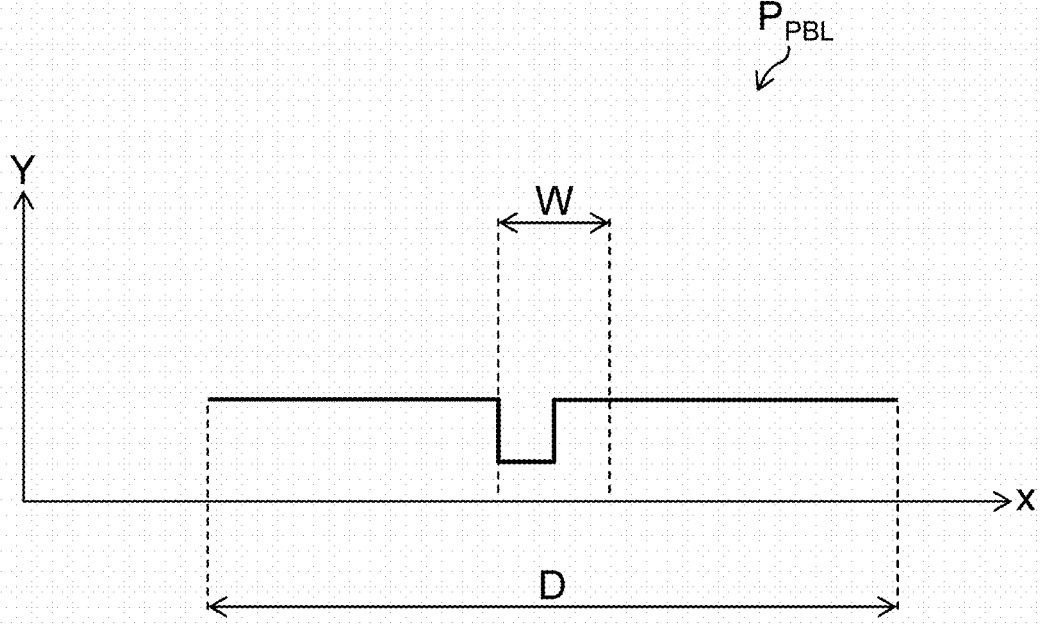

The profile $P_{PAL}$ shown in FIG. 15 is the luminance profile of the left incident image of the tablet T placed at the position A, along the x-axis direction passing through the center of the tablet T in the xy-plan view. The profile $P_{PBL}$ shown in FIG. 15 is the luminance profile of the left incident image of the tablet T placed at the position B, along the x-axis direction passing through the center of the tablet T in the xy-plan view. In FIG. 15, the abscissa axis indicates the normalized position in the x-axis direction, and the ordinate axis indicates the luminance value Y. As shown in FIG. 15, the portion corresponding to the upper surface of the tablet T is irradiated with the illumination light $L_L$, and the luminance becomes relatively high accordingly. The right-side surface $S_R$ of the engraved mark S in FIG. 14 is irradiated also with the illumination light $L_L$, and the portion corresponding to a surface $S_R$ becomes relatively high accordingly. On the other hand, the left-side surface $S_L$ of the engraved mark S in FIG. 14 is not irradiated with the illumination light $L_L$, and the portion corresponding to the surface $S_L$ becomes relatively low accordingly.

Furthermore, the distance to the first light source 104 from the position A is smaller than that from the position B. Consequently, the illumination light $L_L$ by the first light source 104 is weaker at the position B than at the position A. Accordingly, the profile $P_{PBL}$ generally has a lower luminance than the profile $P_{PAL}$ shown in FIG. 15.

Subsequently, the imaging control unit 128 turns on only the second light source 106 among the light sources of the irradiating unit 126, and emits illumination light $L_R$ shown in FIG. 14 from the second light source 106 to the tablet T placed on the stage 102. The upper surface of the tablet T is then imaged by the camera 120, and the right incident image is obtained.

Figure 16:
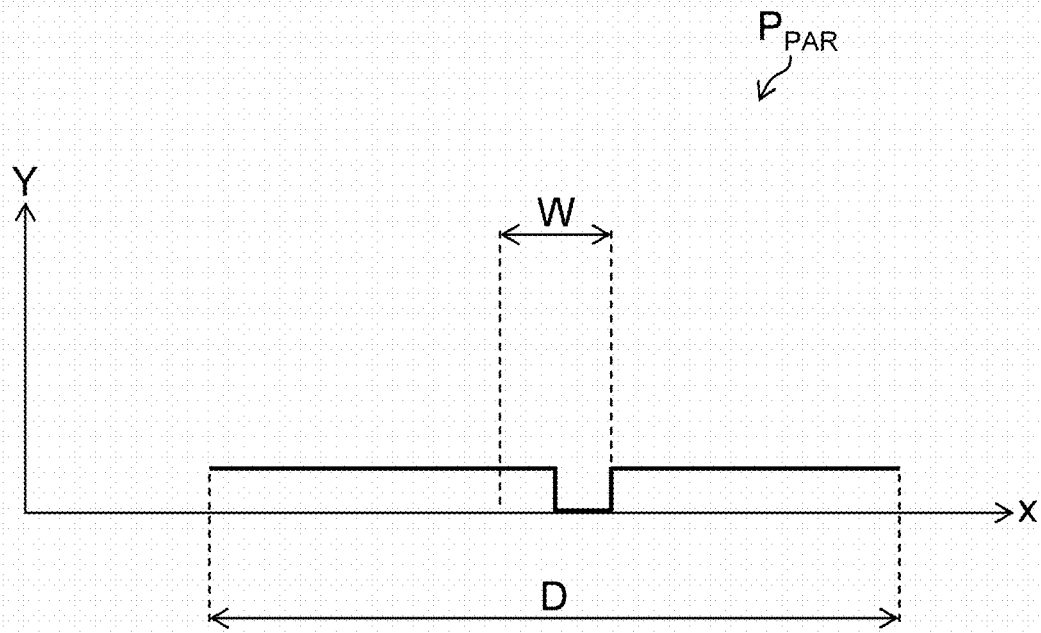
FIG. 16 shows a luminance profile taken along the x-axis direction passing through the center of a right incident image of the tablet in the xy-plan view.
Figure 16:
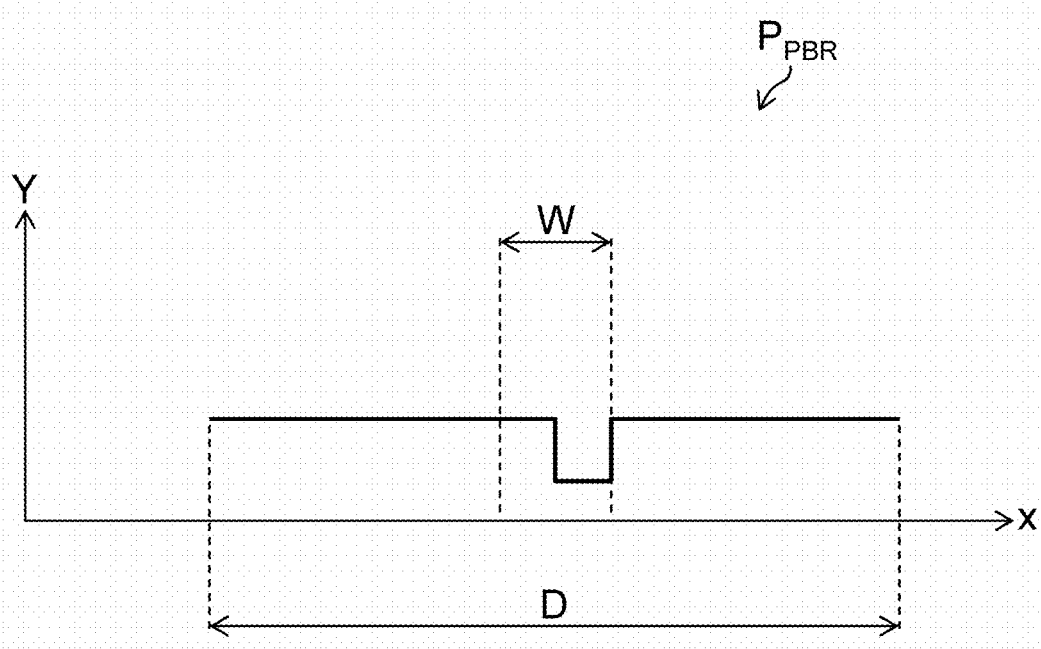

The profile $P_{PAR}$ shown in FIG. 16 is the luminance profile of the right incident image of the tablet T placed at the position, along the x-axis direction passing through the center of the tablet T in the xy-plan view. The profile $P_{PBL}$ shown in FIG. 16 is the luminance profile of the right incident image of the tablet T placed at the position B, along the x-axis direction passing through the center of the tablet T in the xy-plan view. In FIG. 16, the abscissa axis indicates the normalized position in the x-axis direction, and the ordinate axis indicates the luminance value Y. As shown in FIG. 16, the portion corresponding to the upper surface of the tablet T is irradiated with the illumination light $L_R$, and the luminance becomes relatively high accordingly. The left-side surface $S_L$ of the engraved mark S in FIG. 14 is irradiated also with the illumination light $L_R$, and the portion corresponding to a surface $S_L$ becomes relatively high accordingly. On the other hand, the right-side surface $S_R$ of the engraved mark S in FIG. 14 is not irradiated with the illumination light $L_R$, and the portion corresponding to the surface $S_R$ becomes relatively low accordingly.

Furthermore, the distance to the second light source 106 from the position B is smaller than that from the position A. Consequently, the illumination light $L_R$ by the second light source 106 is weaker at the position A than at the position B. Accordingly, the profile $P_{P4R}$ generally has a lower luminance than the profile $P_{PBR}$.

Figure 17:
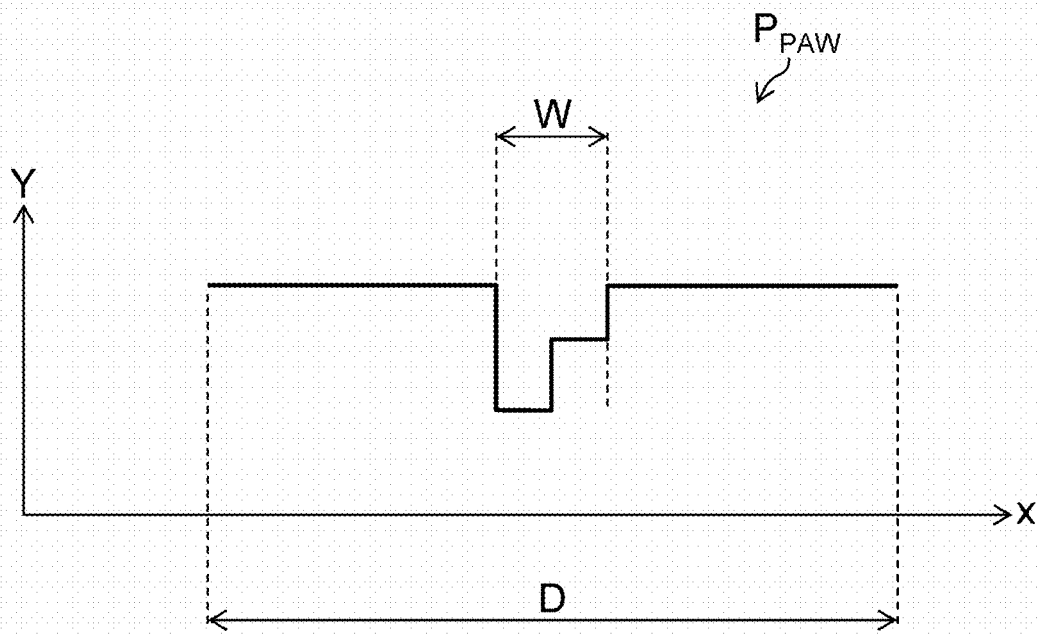
FIG. 17 shows a luminance profile of a composite image of the tablet.
Figure 17:
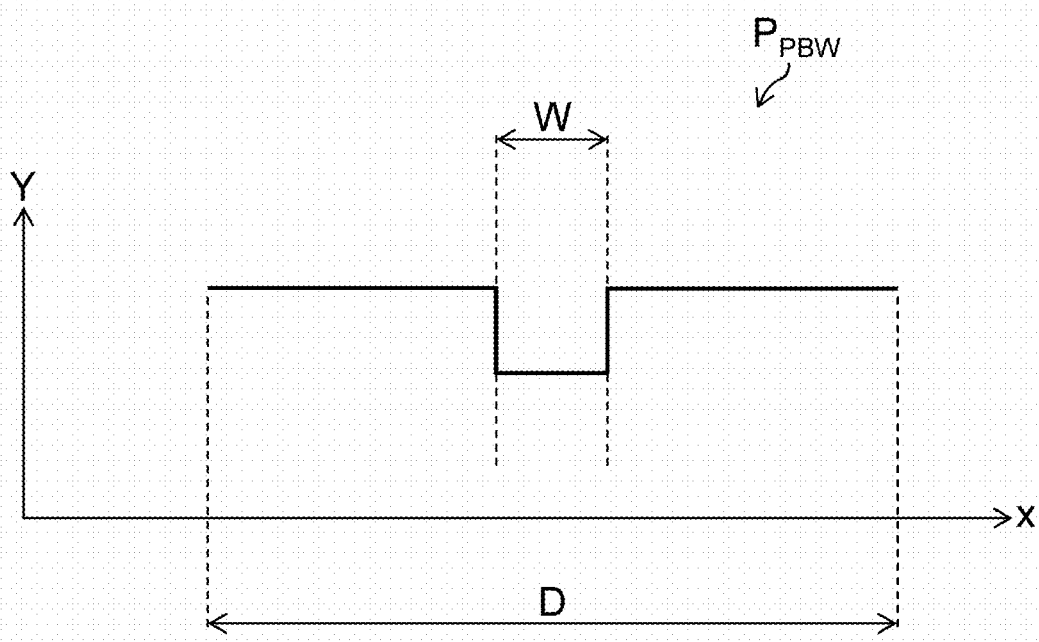

The profile $P_{P4W}$ shown in FIG. 17 is the luminance profile of the composite image obtained by adding up the left incident image and the right incident image of the tablet T at the position A, and is the luminance profile of the tablet T along the x-axis direction passing through the center of the tablet T in the xy-plan view. A distance from the position A to the first light source 104 is relatively small, and a distance from the position A to the second light source 106 is relatively large. Accordingly, in profile $P_{P4W}$, the luminance value at the position of the surface $S_R$ of the engraved mark S is different from the luminance value at the position of the surface $S_L$.

The profile $P_{PBW}$ shown in FIG. 17 is the luminance profile of the composite image obtained by adding up the left incident image and the right incident image of the tablet T at the position B, and is the luminance profile of the tablet T along the x-axis direction passing through the center of the tablet T in the xy-plan view. At the position B, the distance to the first light source 104 and the distance to the second light source 106 are the same as each other. Accordingly, in the profile $P_{PBW}$, the luminance value at the position of the surface $S_R$ is the same as the luminance value at the position of the surface $S_L$.

Thus, it is understood that the taken image of the tablet T has luminance profiles varying according to the positional relationship between the light source and the engraved mark. As a result, images of different shadows are obtained. Accordingly, the robustness in image collation decreases.

Further, even if the luminance profiles are compared with each other, the correlation decreases. Accordingly, even if a binarizing process, a noise reducing process, an edge extracting process and the like are performed, in a case of application to the composite image of the left incident image and the right incident image, thresholds according to the positions are different from each other. It is difficult to extract only the portion corresponding the engraved mark using a small number of parameters.

Here, the example of extracting the luminance profile from the taken image has been described. Not only for the luminance profile, but also for RGB (Red Green Blue) images and RGB monochromatic images, a similar problem occurs. The same applies to images converted into a CIE (Commission Internationale de l'Eclairage) XYZ color system, a CIELuv (L* u* v*) color system, an HSV (Hue, Saturation, Value) color space, and an LCH (Light, Color, Hue) color space.

[Image Processing Method]

An image processing method of extracting an engraved mark S added to the surface of the tablet T according to the fourth embodiment is described.

As described above, the imaging control unit 128 turns on only the first light source 104 among the light sources of the irradiating unit 126, images the upper surface of the tablet T by the camera 120, and obtains the left incident image. Further, the imaging control unit 128 turns on only the second light source 106 among the light sources of the irradiating unit 126, images the upper surface of the tablet T by the camera 120, and obtains the right incident image.

The thus obtained left incident image and right incident image of the tablet T at the position A, and those of the tablet T at the position B are input into the edge image generating unit 182.

The edge image generating unit 182 applies the edge extracting filters in directions in conformity with the emitting directions to the input left incident images and right incident images, and generates left edge images and right edge images. Here, a Sobel filter having a size larger than half (the number of pixels) the width of the groove of the engraved mark S is used as the edge extracting filter. For example, if the number of pixels of the width of the groove of the engraved mark S is four, a Sobel filter having a size (three pixels in the x-axis direction×three pixels in the y-axis direction and the like) larger than two which is half of four. In this embodiment, a shadow is caused by each illumination light in an area that is half the width of the groove. Accordingly, by using the edge extracting filter having a size in consideration of the number of pixels of the edge, it is possible to accurately extract the groove, and reduce information such as a pattern, a scar and the like on a surface, which are other than the engraved mark and smaller than the width of the groove.

Note that the edge extracting filter process can include at least one among a Sobel filter process, a Laplacian filter process, and a Canny filter process. The edge extracting filter process can be appropriately selected according to the method of collation with the master image.

The direction in conformity with the emitting direction means a direction of the emitting direction in the xy-plan view here. That is, the direction of the emitting direction of the illumination light from the first light source 104 in the xy-plan view is a direction from the left to the right (rightward direction) in FIG. 11. The direction of the emitting direction of the illumination light from the second light source 106 in the xy-plan view is a direction from the right to the left (leftward direction) in FIG. 11.

Figure 18:
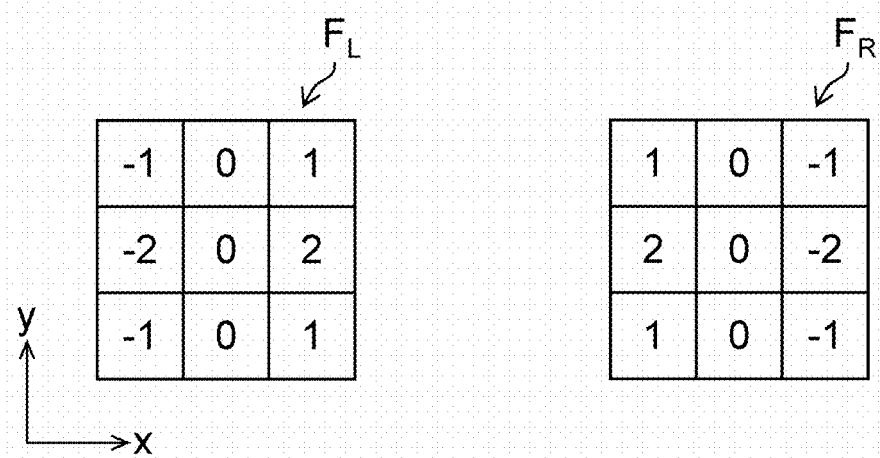
FIG. 18 shows a left directional Sobel filter and a right directional Sobel filter.

FIG. 18 shows a Sobel filter used for the Sobel filter process in each direction, and shows a left directional Sobel filter $F_L$ and a right directional Sobel filter $F_R$. In this embodiment, the resolution of each of the left incident image and the right incident image is 360 dpi. The sizes corresponding to half the number of pixels of the engraved mark S are: 3 pixels×3 pixels in the x-axis direction and y-axis direction; 5 pixels×5 pixels in the x-axis direction and the y-axis direction; or 7 pixels×7 pixels in the x-axis direction and the y-axis direction. If the resolution is different from this example, a filter having a size larger than half the number of pixels of the width of the groove of the engraved mark S may be appropriately selected. Here, the Sobel filter of 3 pixels×3 pixels in the x-axis direction and y-axis direction is used.

Figure 19:
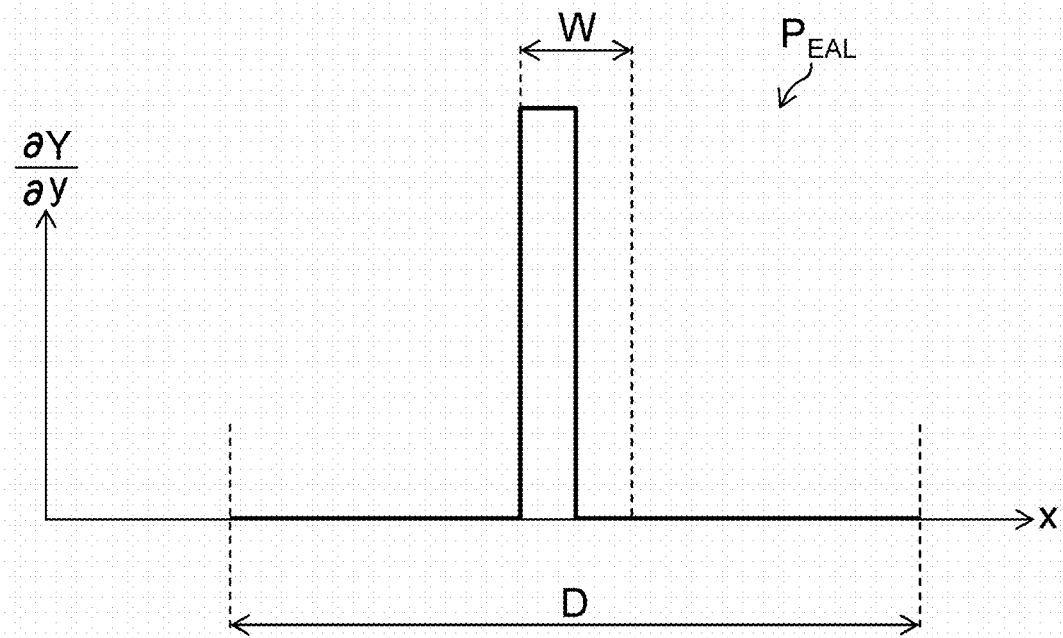
FIG. 19 shows a differential profile of the profile shown in FIG. 15.
Figure 19:
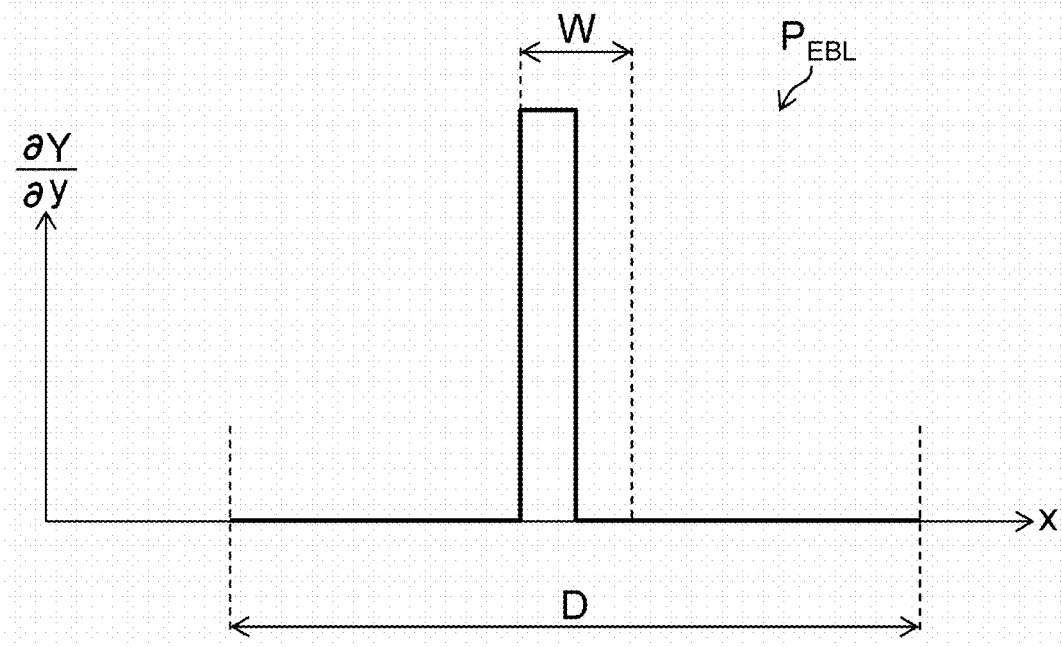

The edge image generating unit 182 applies an edge detecting process using the Sobel filter $F_L$ to the left incident image of the tablet T at the position A, and generates a left edge image. The profile $P_{EAL}$ shown in FIG. 19 is the differential profile of the profile $P_{P4L}$ shown in FIG. 15, and is equivalent to the luminance profile of the left edge image of the tablet T at the position A, along the x-axis direction passing through the center of the tablet T in the xy-plan view.

The edge image generating unit 182 applies an edge detecting process using the Sobel filter $F_L$ to the left incident image of the tablet T at the position B, and generates a left edge image. The profile $P_{EBL}$ shown in FIG. 19 is the differential profile of the profile $P_{PBL}$ shown in FIG. 15, and is equivalent to the luminance profile of the left edge image of the tablet T at the position B, along the x-axis direction passing through the center of the tablet T in the xy-plan view.

Figure 20:
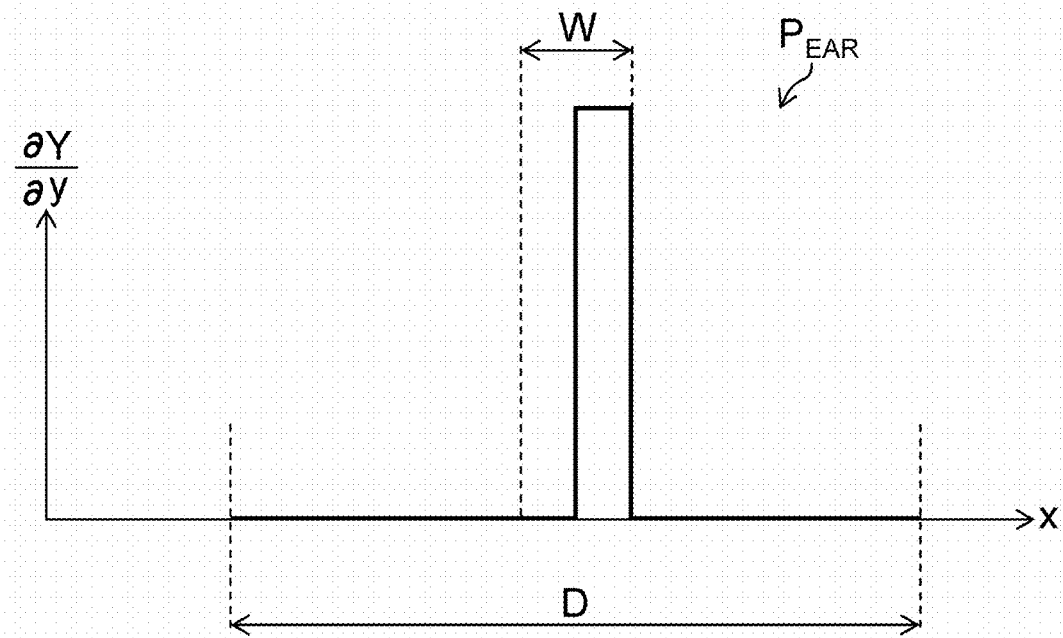
FIG. 20 shows a differential profile of the profile shown in FIG. 15.
Figure 20:
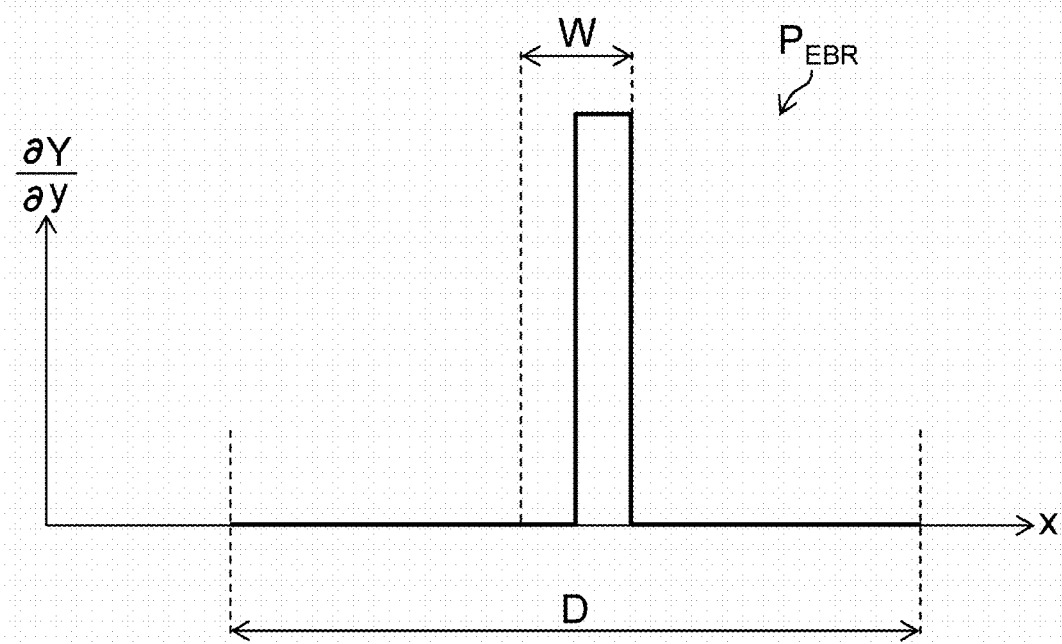

Likewise, the edge image generating unit 182 applies an edge detecting process using the Sobel filter $F_R$ to the right incident image of the tablet T at the position A, and generates a right edge image. The profile $P_{EAL}$ shown in FIG. 20 is the differential profile of the profile $P_{PAL}$ shown in FIG. 16, and is equivalent to the luminance profile of the right edge image of the tablet T at the position A, along the x-axis direction passing through the center of the tablet T in the xy-plan view.

Furthermore, the edge image generating unit 182 applies an edge detecting process using the Sobel filter $F_R$ to the right incident image of the tablet T at the position B, and generates a right edge image. The profile $P_{EBL}$ shown in FIG. 20 is the differential profile of the profile $P_{PBL}$ shown in FIG. 16, and is equivalent to the luminance profile of the right edge image of the tablet T at the position B, along the x-axis direction passing through the center of the tablet T in the xy-plan view.

Lastly, the image composing unit 184 composes the left edge image and the right edge image with each other and generates a composite image.

Figure 21:
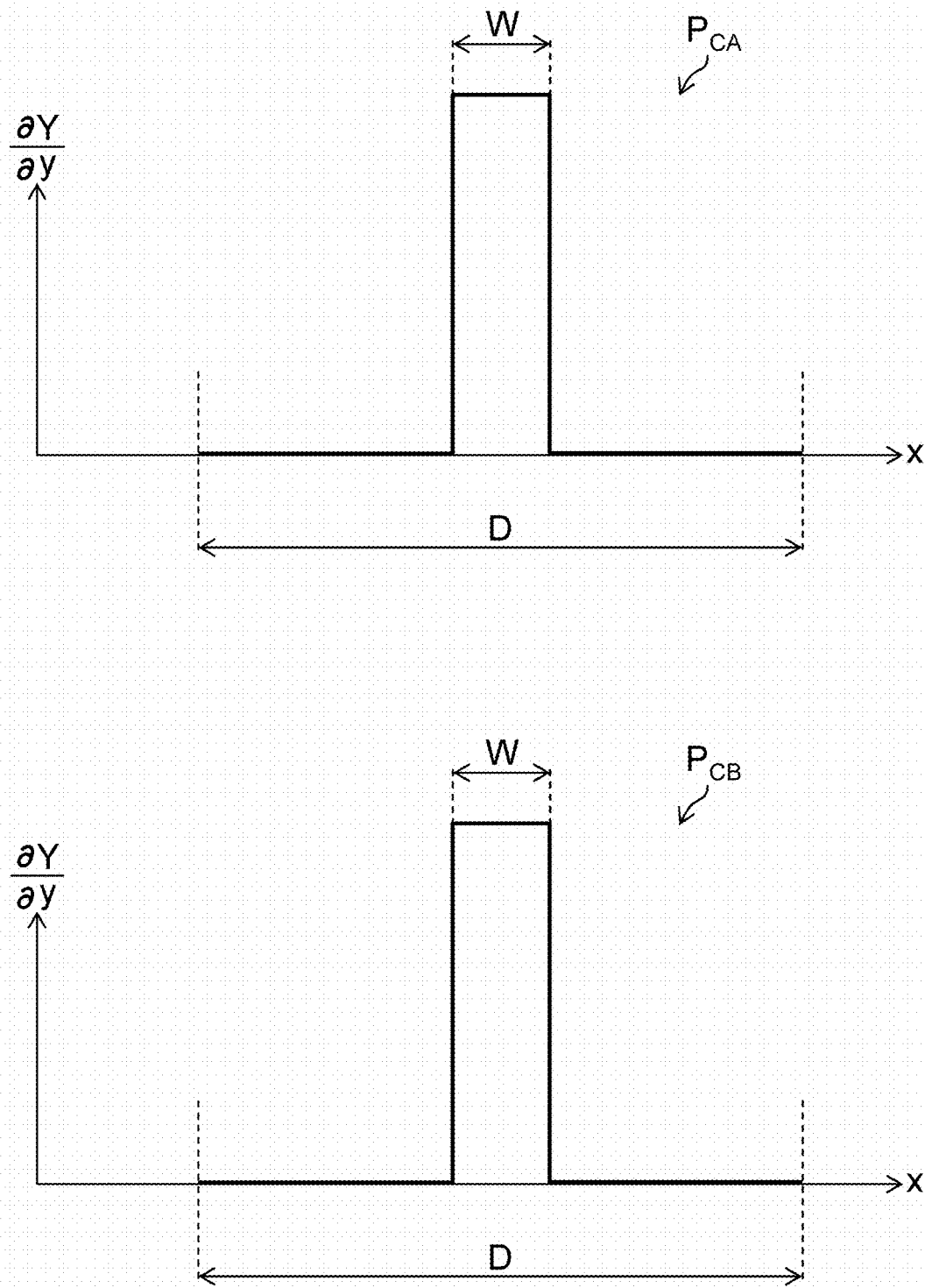
FIG. 21 shows a composite profile of the profiles shown in FIGS. 19 and 20.

A profile $P_{CA}$ shown in FIG. 21 is a composite profile of the profile $P_{EAL}$ and the profile $P_{EAR}$, and is equivalent to the luminance profile of the composite image of the left edge image and the right edge image of the tablet T at the position A, along the x-axis direction passing through the center of the tablet T in the xy-plan view.

A profile $P_{CB}$ shown in FIG. 21 is a composite profile of the profile $P_{EBL}$ and the profile $P_{EBR}$, and is equivalent to the luminance profile of the composite image of the left edge image and the right edge image of the tablet T at the position B, along the x-axis direction passing through the center of the tablet T in the xy-plan view.

As shown in FIG. 21, the luminance profile of the composite image has a higher S/N ratio (signal-to-noise ratio) at the portion of the engraved mark S in comparison with the luminance profile shown in FIG. 17.

As described above, by extracting the edge, the signal of the pattern or the like that is not dependent on the direction of the illumination (causes no shadow) relatively decreases. Accordingly, it is possible to extract the engraved mark while reducing the information such as a pattern, a scar and the like on a surface of the drug, which are other than the engraved mark and smaller than the groove of the engraved mark.

<Fifth Embodiment>

The fourth embodiment describes the example where the left incident image and the right incident image are used, as two images in which the light emitting directions to the surface of the tablet T are different from each other. It is preferable that the light emitting directions be three or more directions. This embodiment describes an example where the light emitting directions are four directions and four images are used.

[Image Processing Method]

Here, it is assumed that the tablet T is placed on the mounting surface 102A of the stage 102 of the drug identification device 180, with the engraved mark S being oriented on the upper side in the vertical direction.

First, the imaging control unit 128 obtains the upper incident images, right incident images, left incident images and lower incident images of the upper surface and the lower surface of the tablet T (an example of an obtaining step).

That is, the imaging control unit 128 turns on only the third light source 108 and the seventh light source 116 among the light sources of the irradiating unit 126, and obtains the upper incident images of the upper surface and the lower surface of the tablet T by the camera 120 and the camera 122. Likewise, the imaging control unit 128 turns on only the second light source 106 and the sixth light source 114 among the light sources of the irradiating unit 126 and obtains the right incident images of the upper surface and the lower surface of the tablet T by the camera 120 and the camera 122, turns on only the first light source 104 and the fifth light source 112 among the light sources of the irradiating unit 126 and obtains the left incident images of the upper surface and the lower surface of the tablet T by the camera 120 and the camera 122, and turns on only the fourth light source 110 and the eighth light source 118 among the light sources of the irradiating unit 126 and obtains the lower incident images of the upper surface and the lower surface of the tablet T by the camera 120 and the camera 122.

The thus obtained upper incident images, right incident images, left incident images and lower incident images are input into the edge image generating unit 182.

Figure 22:
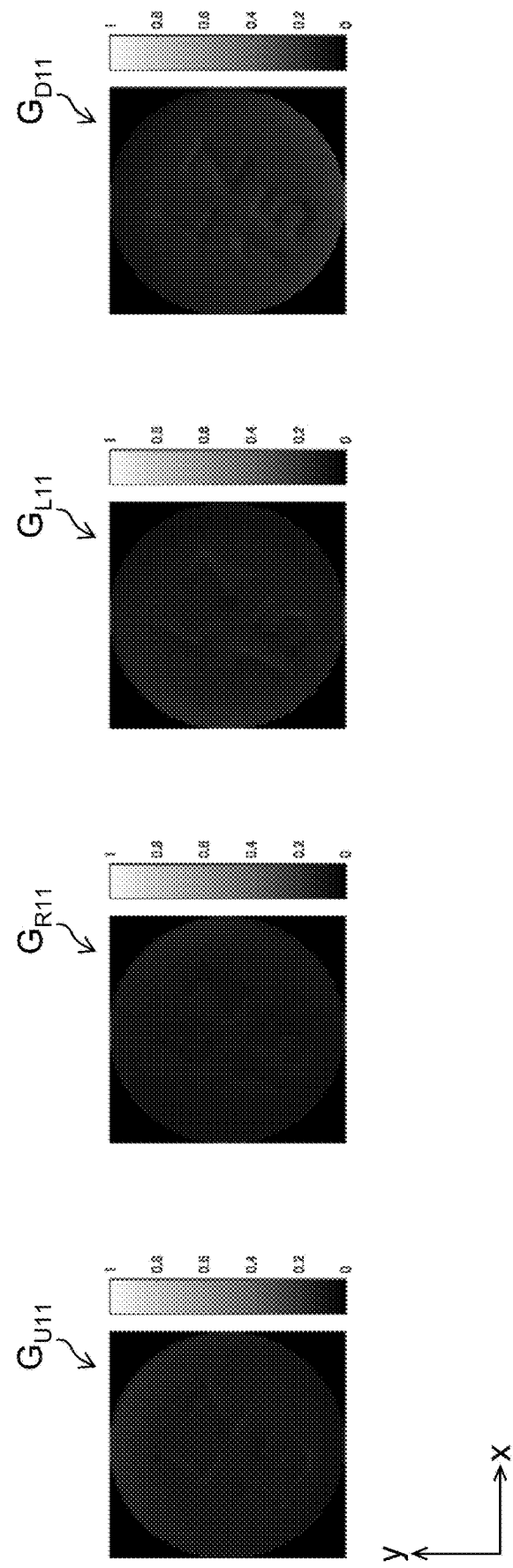
FIG. 22 shows examples of an upper incident image, a right incident image, a left incident image and a lower incident image, and the ranges of luminance values of the images.

The edge image generating unit 182 extracts images in which the engraved mark S has been taken, from among the input upper incident images, right incident images, left incident images and lower incident images. Here, the engraved mark S has been imaged by the camera 120. FIG. 22 shows examples of the upper incident image $G_{U11}$, the right incident image $G_{R11}$, the left incident image $G_{L11}$, and the lower incident image $G_{D11}$, and the range of luminance value of each image, which have been taken by the camera 120, among the upper incident images, the right incident images, the left incident images, and the lower incident images, which have been obtained by the obtaining unit 124.

Figure 23:
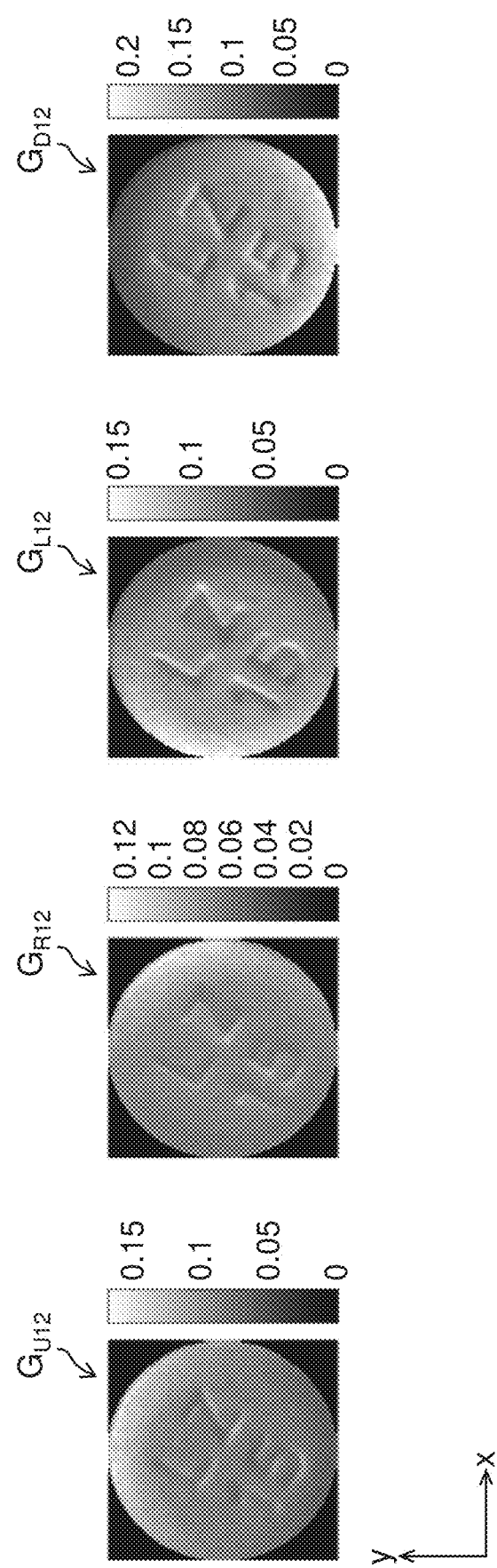
FIG. 23 shows examples of an upper incident image, a right incident image, a left incident image and a lower incident image after adjustment of the ranges of the luminance values, and the ranges of adjusted luminance values.

Subsequently, the edge image generating unit 182 adjusts the ranges of the luminance values of the upper incident image $G_{U11}$, the right incident image $G_{R11}$, the left incident image $G_{L11}$ and the lower incident image $G_{D11}$ to ranges that allow the engraved mark S to be visible. FIG. 23 shows examples of an upper incident image $G_{U12}$, a right incident image $G_{R12}$, a left incident image $G_{L12}$ and a lower incident image $G_{D12}$ after adjustment of the ranges of the luminance values, and the ranges of adjusted luminance values.

Here, the edge image generating unit 182 may apply the luminance irregularity correcting process to each of the upper incident image $G_{U12}$, the right incident image $G_{R12}$, the left incident image $G_{L12}$, and the lower incident image $G_{D12}$. For example, the luminance irregularity correcting process divides the upper incident image $G_{U12}$, the right incident image $G_{R12}$, the left incident image $G_{L12}$ and the lower incident image $G_{D12}$, by respective images obtained by applying the Gaussian filter process to the upper incident image $G_{U12}$, the right incident image $G_{R12}$, the left incident image $G_{L12}$ and the lower incident image $G_{D12}$.

Next, the edge image generating unit 182 applies the edge extracting filters that are in directions in conformity with the emitting direction of the illumination lights and have a size in conformity with the number of pixels of the width of the groove of the engraved mark S to the upper incident image $G_{U12}$, the right incident image $G_{R12}$, the left incident image $G_{L12}$ and the lower incident image $G_{D12}$, respectively. Here, as with the fourth embodiment, the Sobel filter having a size larger than half the number of pixels of the width of the groove of the engraved mark S, is used as the edge extracting filter.

In this embodiment, the direction in conformity with the emitting direction includes the direction of the emitting direction of the illumination light in the xy-plan view, the direction inclined by 45 degrees in the xy-plan view from the emitting direction in the xy-plan view, and the direction inclined by −45 degrees in the xy-plan view from the emitting direction in the xy-plan view. This is because the illumination light from each light source of the irradiating unit 126 is not complete parallel light, and in order to detect the engraved mark in the direction inclined from each emitting direction.

Note that as with the fourth embodiment, the direction in conformity with the emitting direction may be only the direction of the emitting direction in the xy-plan view.

Figure 24:
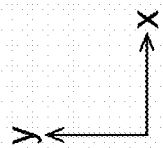
FIG. 24 shows an upper directional Sobel filter, an upper right directional Sobel filter, an upper left directional Sobel filter, a lower directional Sobel filter, a lower right directional Sobel filter, and a lower left directional Sobel filter.

FIG. 24 shows Sobel filters used for the Sobel filter processes in the respective directions, that is, the upper directional Sobel filter $F_U$, the upper right directional Sobel filter $F_{UR}$, the upper left directional Sobel filter $F_{UL}$, the lower directional Sobel filter $F_D$, lower right directional Sobel filter $F_{DR}$, and the lower left directional Sobel filter $F_{DL}$. The left directional Sobel filter $F_L$ and the right directional Sobel filter $F_R$, which are shown in FIG. 18, are also used.

To the upper incident image $G_{U12}$, the edge image generating unit 182 applies the upper directional Sobel filter $F_U$ to generate an edge image, applies the upper right directional Sobel filter $F_{UR}$ to generate an edge image, and applies the upper left directional Sobel filter $F_{UL}$ to generate an edge image, and adds up the three edge images to generate an upper directional edge image $G_{U13}$.

Likewise, to the right incident image $G_{R12}$, the edge image generating unit 182 applies the right directional Sobel filter $F_R$, the upper right directional Sobel filter $F_{UR}$ and the lower right directional Sobel filter $F_{DR}$, to generate a right directional edge image $G_{R13}$.

Furthermore, to the left incident image $G_{L12}$, the edge image generating unit 182 applies the left directional Sobel filter $F_L$, the upper left directional Sobel filter $F_{UL}$ and the lower left directional Sobel filter $F_{DL}$, to generate a left directional edge image $G_{L13}$.

Moreover, to the lower incident image $G_{D12}$, the edge image generating unit 182 applies the lower directional Sobel filter $F_D$, the lower right directional Sobel filter $F_{DR}$ and the lower left directional Sobel filter $F_{DL}$, to generate a lower directional edge image $G_{D13}$ (an example of an edge image generating step, and an example of an edge image generating function).

Figure 25:
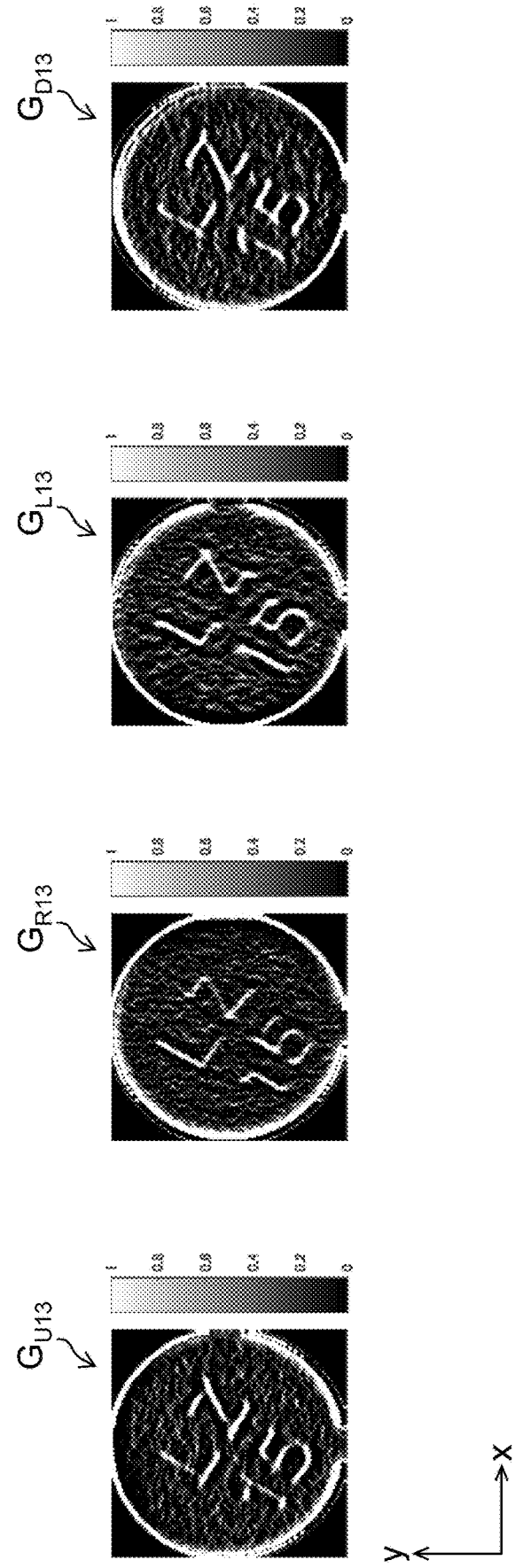
FIG. 25 shows examples of an upper directional edge image, a right directional edge image, a left directional edge image, and a lower directional edge image.

FIG. 25 shows examples of the upper directional edge image $G_{U13}$, the right directional edge image $G_{R13}$, the left directional edge image $G_{L13}$ and the lower directional edge image $G_{D13}$. As shown in FIG. 25, each edge image is represented such that the extracted edge portion has a high luminance (white).

The edge image generating unit 182 may be configured to apply the noise reducing process (smoothing process) to each of the upper directional edge image $G_{U13}$, the right directional edge image $G_{R13}$, the left directional edge image $G_{L13}$ and the lower directional edge image $G_{D13}$. The noise reducing process can include at least one among a median filter process, a Gaussian filter process, a non-local means filter process and a Wiener filter process, and can be appropriately selected according to the method of collation with the master image.

The thus generated upper directional edge image $G_{U13}$, right directional edge image $G_{R13}$, left directional edge image $G_{L13}$ and lower directional edge image $G_{D13}$ are input into the image composing unit 184.

Figure 26:
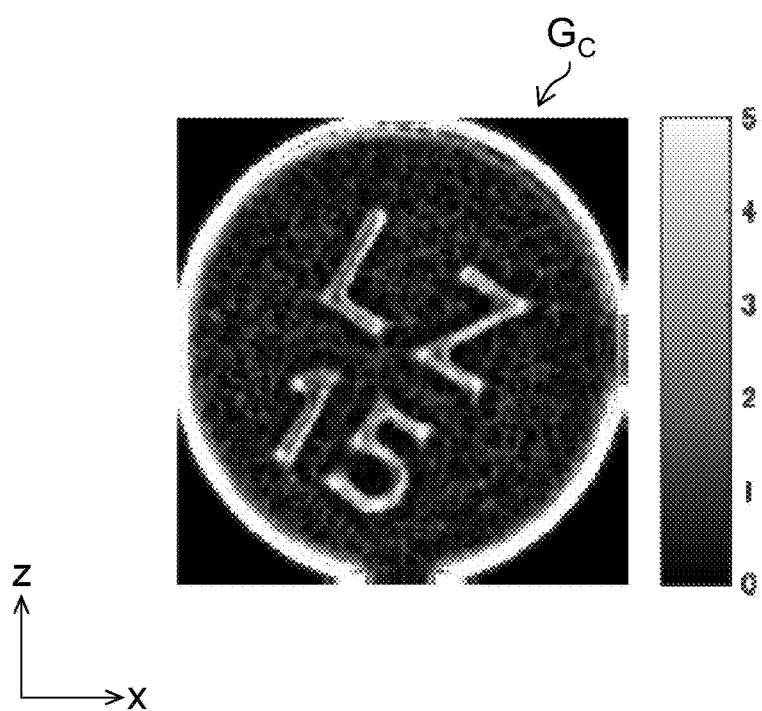
FIG. 26 shows an example of the composite image, and the range of the luminance values.

The image composing unit 184 adds up the upper directional edge image $G_{U13}$, the right directional edge image $G_{R13}$, the left directional edge image $G_{L13}$ and the lower directional edge image $G_{D13}$ to generate a composite image $G_C$ (an example of an image composing step, and an example of an image composing function). FIG. 26 shows an example of the composite image $G_C$ and the range of the luminance value. As shown in FIG. 26, the range of the luminance of the composite image $G_C$ is enlarged, and the luminance of the portion of the engraved mark S is relatively high. Accordingly, the luminance of a pattern, a scar and the like which are other than the portion of the engraved mark S and are independent of the illumination direction (without causing a shadow), is relatively low. Consequently, the gradation information of a pattern, a scar and the like on the surface of the drug, which are other than the engraved mark and smaller than the width of the groove of the engraved mark, does not remain.

As described above, it is possible to reduce information such as the pattern and the like which are information other than the engraved mark S. Accordingly, information other than the engraved mark S is not obtained as information on the tablet T. Consequently, the engraved mark S can be accurately extracted, and collation with the master image can be appropriately performed.

Note that the image composing unit 184 may be configured to multiply together the upper directional edge image $G_{U13}$, the right directional edge image $G_{R13}$, the left directional edge image $G_{L13}$ and the lower directional edge image $G_{D13}$, to generate the composite image $G_C$. The composing method can be appropriately selected according to the method of collation with the master image.

As described above, even if the positional relationship between the light source and the engraved mark is haphazardly determined, the engraved mark S added on the surface of the tablet T can be appropriately extracted. Accordingly, the robustness in collation of the tablet can be improved.

Here, the example is described where the number of emitting directions of the illumination light is four. Alternatively, five or more directions may be adopted. The more the number of emitting directions of the illumination light is, the higher the detection accuracy is. The number of emitting directions may be appropriately determined based on the required detection accuracy, operation process time and the like.

It is preferable that the fourth to fifth embodiments accurately extracting the engraved mark be executed in a case where it is determined that the identification information has been added by mark engraving in the first to third embodiments. If it is determined that the identification information has been added by character printing in the first to third embodiments, it may be possible to perform a noise reducing process and sharpening process for accurately extracting the printed character from the taken image.

<Sixth Embodiment>

The configuration of determining whether the identification information is added by mark engraving or by character printing according to the first to third embodiments, and the configuration of extracting the engraved mark according to the fourth to fifth embodiments can be applied to a drug identification device and a drug inspection assistance device described below.

[Configuration of Drug Identification Device]

Figure 27:
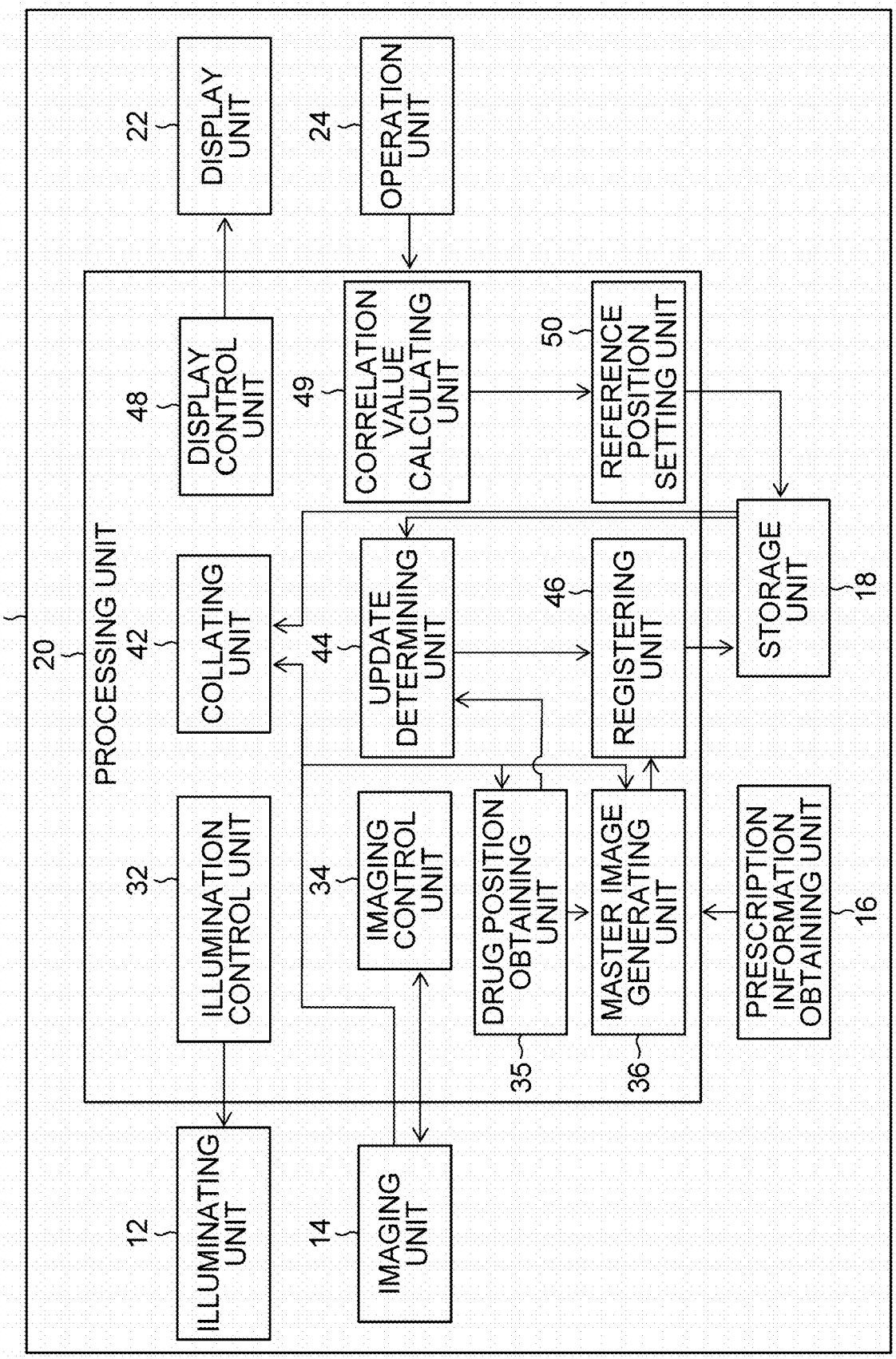
FIG. 27 is a block diagram showing an internal configuration of a drug identification device.

FIG. 27 is a block diagram showing an internal configuration of a drug identification device 10 according to a sixth embodiment. The drug identification device 10 is configured to include: an illuminating unit 12 that illuminates a packed drug; an imaging unit 14 that images the drug illuminated by the illuminating unit 12; a prescription information obtaining unit 16 that obtains prescription information indicating a prescription of the drug for a user; a storage unit 18 that stores a program and information required to execute the program; a processing unit 20 that performs various processes according to the program stored in the storage unit 18; a display unit 22 that can display an image; and an operation unit 24 that receives an operation from the user.

The "packing" (packaging) of the drug includes one dose packaging. The "one dose packaging" means packaging prescribed (dispensed) drugs in a divided manner on a single dose basis. There are a case where different kinds of drugs are packaged in a single chartula, a case where a plurality of drugs of the same kind are packaged in a single chartula, and a case where only a single drug is packaged in a single chartula, pursuant to the prescription details. Modes of drugs to be packed in a single chartula may be, for example, a tablet and a capsule. However, the modes are not specifically limited. Examples of materials of chartulae include paper and plastic. However, the materials are not specifically limited. "Packing" (or "packaging") is not limited to a case of packing in a divided manner on a single dose basis. It is only required that the drug is packaged in a chartula.

The illuminating unit 12 is configured to include light sources. The light sources of the illuminating unit 12 may be at least one of the first light source 104, the second light source 106, the third light source 108, the fourth light source 110, the fifth light source 112, the sixth light source 114, the seventh light source 116 and the eighth light source 118, which have thus been described. The mounting-surface-side dome lamp 142, the rear-surface-side dome lamp 148, the first epi-illumination lamp 162, and the second epi-illumination lamp 168 may be used.

The imaging unit 14 is configured to include a camera (cameras). At least one of the camera 120 and the camera 122, which have thus been described, can be adopted as the cameras of the imaging unit 14.

The prescription information obtaining unit 16 obtains prescription information by optically reading characters described on a prescription, for example. The prescription information may be obtained by reading a bar code (or a two-dimensional code) added to a prescription. Alternatively, prescription information input by a doctor through a computer device may be obtained via communication.

The storage unit 18 is a drug database that includes a transitory storage device and a non-transitory storage device. The storage unit 18 stores master images that indicate drugs, for each kind of drug.

The processing unit 20 includes a CPU (Central Processing Unit), for example. The processing unit 20 has a function of updating the master image stored in the storage unit 18. When a specific condition described later is satisfied, the processing unit 20 performs a master updating process of updating the master image stored in the storage unit 18 using the taken image obtained by the imaging unit 14.

The processing unit 20 is configured to include: an illumination control unit 32 that controls illumination of the illuminating unit 12; an imaging control unit 34 that controls imaging by the imaging unit 14; a drug position obtaining unit 35 that obtains the position of the drug based on the taken image obtained by the imaging unit 14; a master image generating unit 36 that generates the master image from the drug area in the taken image obtained by the imaging unit 14; a collating unit 42 that collates the drug area in the taken image obtained by imaging the drug by the imaging unit 14, with master images stored in the storage unit 18; an update determining unit 44 that determines whether to update the master image or not based on the position of the drug obtained by the drug position obtaining unit 35; a registering unit 46 that registers the master image generated by the master image generating unit 36 if it is determined to update the master image by the update determining unit 44; and a display control unit 48 that controls display of the display unit 22.

It may be possible to provide a correlation value calculating unit 49 that calculates the correlation value indicating the correlation degree between the master image and the drug area in the taken image, or the correlation value between drug areas, and a reference position setting unit 50 that sets a reference position.

The imaging control unit 128, which has been described above, can be adopted as the illumination control unit 32 and the imaging control unit 34 of the processing unit 20. The image comparing unit 130 and the edge image generating unit 182, which have been described above, can be adopted as the drug position obtaining unit 35.

[Package]

Figure 28:
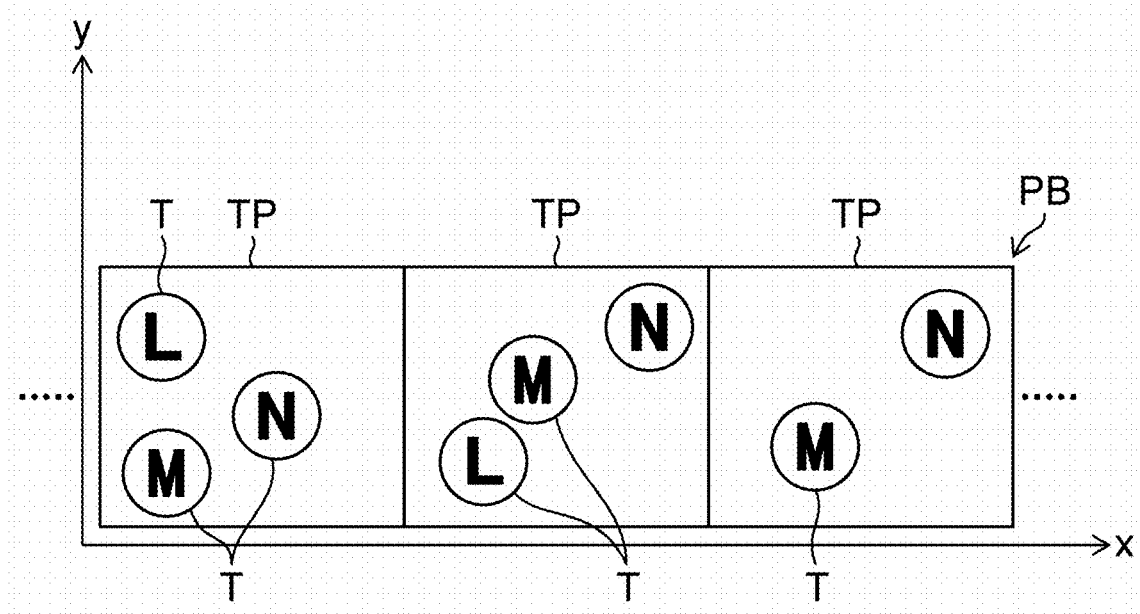
FIG. 28 shows a strip package that includes consecutive packages each containing tablets.

FIG. 28 shows a strip package PB that includes multiple packages TP each packing tablets T of drug, in series. The strip package PB can be conveyed along the x-axis direction. To the tablet T, identification information is added by mark engraving or character printing to indicate the kind of the tablet T. Here, an example is shown where "L," "M" or "N" is engraved on each tablet T.

Preferably, the chartulae of the packages TP have transparent (including translucent; the same applies below) surfaces on both the sides. Character printing or matting may be applied onto one surface of the chartulae material of the packages TP.

The series of packages TP can be conveyed for each size of one package TP in the x-axis direction. The positions of the packages TP may be detectable for each package TP.

Note that this embodiment is not limited to the case where the packages TP are conveyed. Alternatively, a case may be adopted where the packages TP are just placed on a mount or the like.

Figure 29:
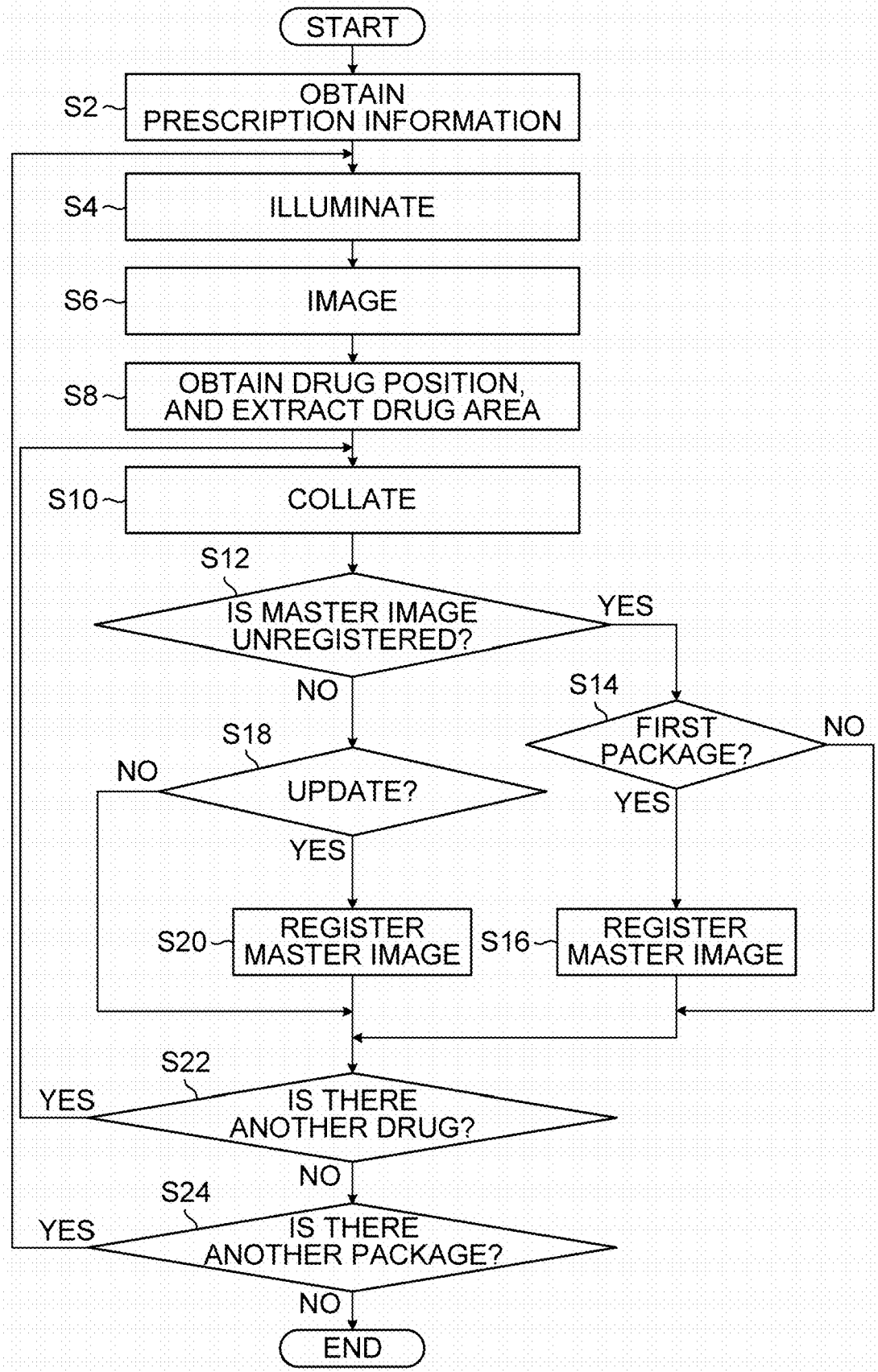
FIG. 29 is a flowchart showing an example of processes of a drug identification method.

FIG. 29 is a flowchart showing an example of processes of a drug identification method according to the sixth embodiment. The processes are executed according to a program by the CPU constituting the processing unit 20 of the drug identification device 10.

First, the prescription information is obtained by the prescription information obtaining unit 16 (step S2).

Next, the separately packed drug is illuminated by the illuminating unit 12 (step S4). The drug illuminated by the illuminating unit 12 is imaged by the imaging unit 14 (step S6). The drug position is obtained by the drug position obtaining unit 35, and the drug area is extracted from the taken image by the master image generating unit 36 (step S8).

Subsequently, a master image stored in the storage unit 18 and the drug area in the taken image are collated with each other by the collating unit 42 (step S10).

The first to third embodiments are applicable to determine whether the identification information is added by mark engraving or by character printing based on the extracted drug area, in order to reduce the number of candidates in the collation process.

In addition, the methods described in the four to fifth embodiments can be used to accurately extract the engraved mark in the extracted drug area.

Next, it is determined whether the master image is an unregistered drug or not (step S12). If the master image is the unregistered drug (if YES in step S12), it is further determined whether the drug is in the first package or not (step S14). If the master image is the unregistered drug and the drug is in the first package (if YES in step S14), the image of the drug area extracted from the taken image is registered as the master image by the registering unit 46 (step S16).

If the master image is a registered drug (if NO in step S12), it is determined by the update determining unit 44 whether to update the master image or not based on the distance between the reference position (e.g., the central position) of the imaging area and the position of the drug (step S18).

If the master image is determined to be updated (if YES in step S18), the image of the drug area extracted from the taken image is registered as the master image by the registering unit 46 (step S20).

It is determined whether there is another drug in the package or not (step S22). If there is another drug in the package (if YES in step S22), the processing returns to step S10, and a process of collating the other drug in the package is performed.

If a drug recognizing process has been performed for all the drugs in the package and any other drug is not in the package (if NO in step S22), it is determined whether there is another package or not (step S24). If another package is present, the processing returns to step S4.

Note that, in a case where multiple drugs are included in a single package, the update determining unit 44 may be configured to determine whether to update the master image or not based on a distance between drugs. That is, in the case of the engraved mark, if a large drug is present at an adjacent position, a shadow sometimes becomes difficult to occur. Accordingly, it is preferable to determine to update the master image in a case where there isn't another drug around the drug. For example, if the distance between drugs is less than a threshold (or equal to or less than the threshold), a shadow of the engraved mark becomes difficult to occur in the taken image and it is determined not to update the master image accordingly.

In the above description, the case of recognizing the engraved mark on the drug is mainly exemplified and described. Alternatively, characters or symbols printed on the drug may be recognized.

<Seventh Embodiment>

A drug inspection assistance device according to a seventh embodiment inspects drugs dispensed based on prescription data and packed into individual bags (packages), and displays a list table of the drugs.

[Configuration of Drug Inspection Assistance Device]

Figure 30:
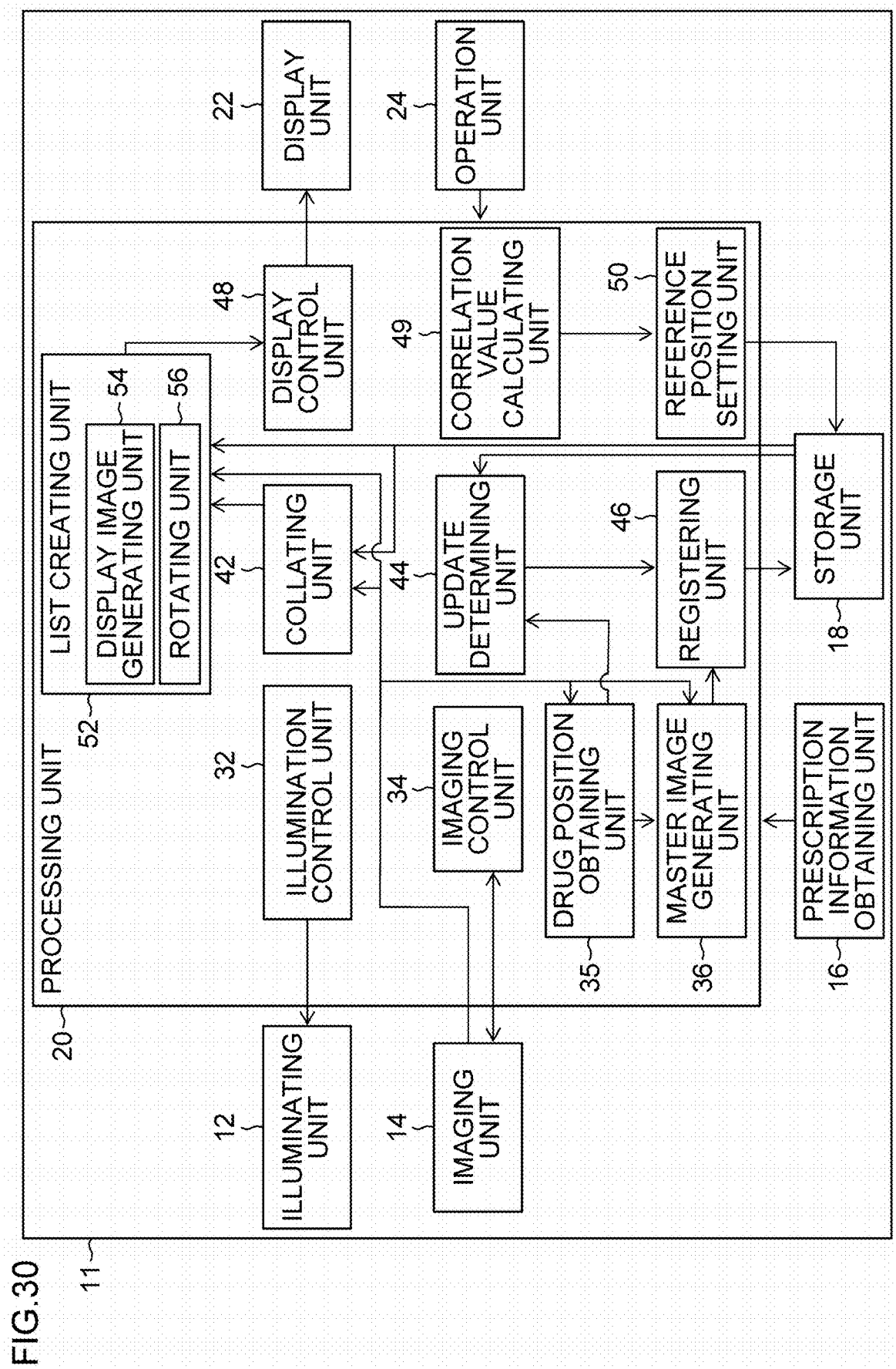
FIG. 30 is a block diagram showing an internal configuration of a drug inspection assistance device.

FIG. 30 is a block diagram showing the internal configuration of a drug inspection assistance device 11 according to the seventh embodiment. Note that the parts common to those of the drug identification device 10 shown in FIG. 27 are assigned the same numerals or characters; their detailed description is omitted.

The collating unit 42 corresponds to a drug discriminating unit. The collating unit 42 collates the master image (an example of a drug master image) stored in the storage unit 18 with the taken image taken by the imaging unit 14, and discriminates which drugs of the master images correspond to drugs in the taken image.

The drug inspection assistance device 11 includes a list creating unit 52. The list creating unit 52 creates a list table of drugs (an example of drugs to be inspected) to be packed into individual bags. The list creating unit 52 obtains an image of the drugs packed in the individual bags, from the imaging unit 14. Here, the list creating unit 52 obtains a drug area image that is a drug area which has been extracted from the taken image by the master image generating unit 36. Further, the list creating unit 52 obtains composite images of drugs packed in the individual bags, which have been adapted to the collating unit 42, from the image composing unit 184. Furthermore, the list creating unit 52 obtains, from the storage unit 18, the master images of drugs which may be dispensed based on the prescription data.

The list creating unit 52 includes a display image generating unit 54 and a rotating unit 56.

For the drug to which the engraved mark has been added, the display image generating unit 54 generates a difference image obtained by subtracting, from the composite image, the drug area image corresponding to the composite image. The difference image is a display image where the engraved mark portion of the drug is enhanced. For the drug to which characters are printed, the display image generating unit 54 generates, as a display image, an image obtained by performing the noise reducing process and the sharpening process to the drug area image.

The rotating unit 56 rotates the display image, thereby aligning the engraved mark portion or the printed character portion of the display image and that of the master image corresponding to the display image in the same orientation.

[Processes of Drug Inspection Assistance Method]

Figure 31:
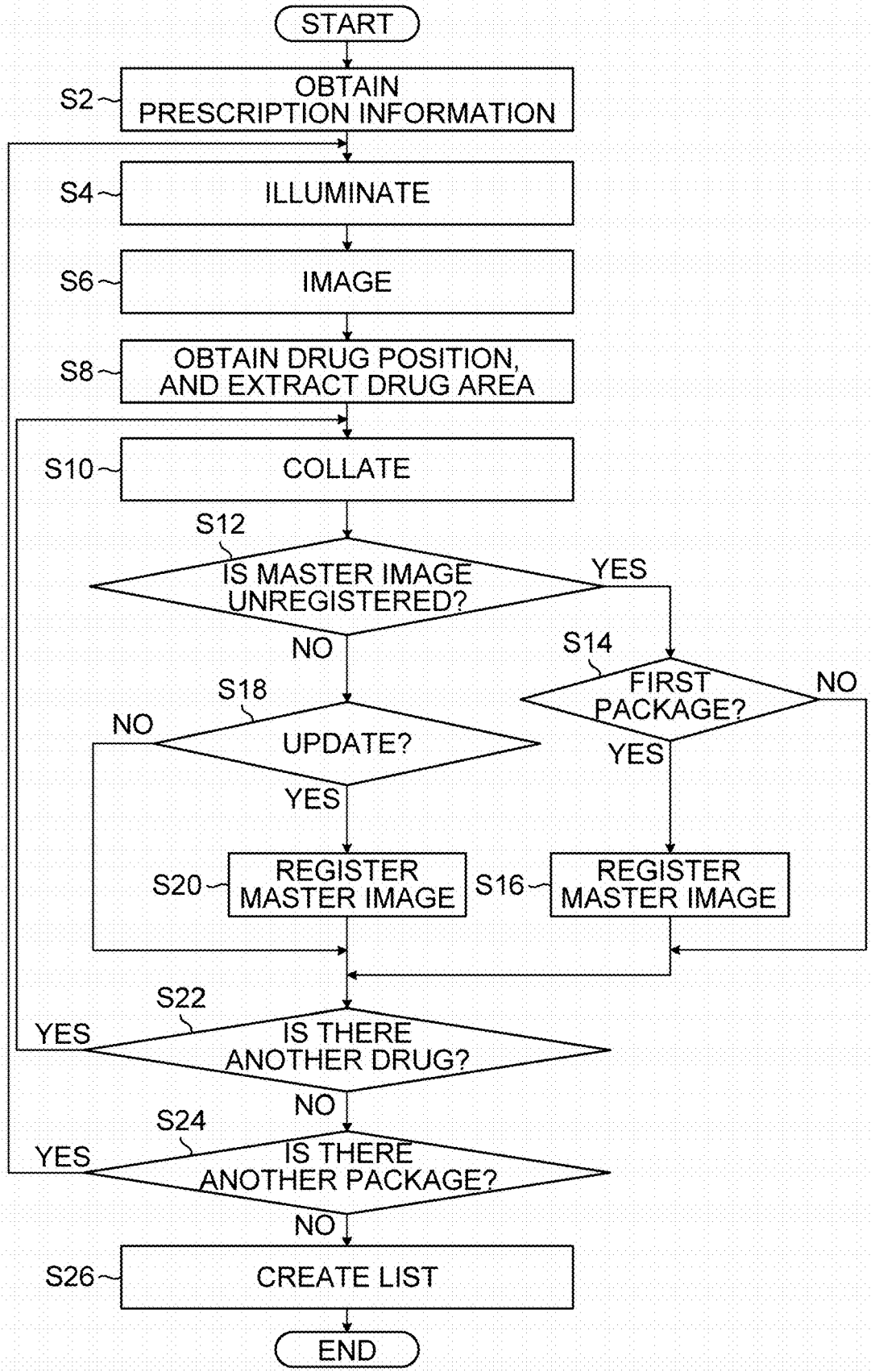
FIG. 31 is a flowchart showing processes of a drug inspection assistance method.

A drug inspection assistance method by the drug inspection assistance device 11 is described. FIG. 31 is a flowchart showing the processes of the drug inspection assistance method. The processes in step S2 to S24 are analogous to those of the flowchart shown in FIG. 29.

In a case where it is determined that the processes have been performed to all the packages in step S24, the processing transitions to step S26. In step S26, the list creating unit 52 creates a list table, and displays the created list table on the display unit 22.

Figure 32:
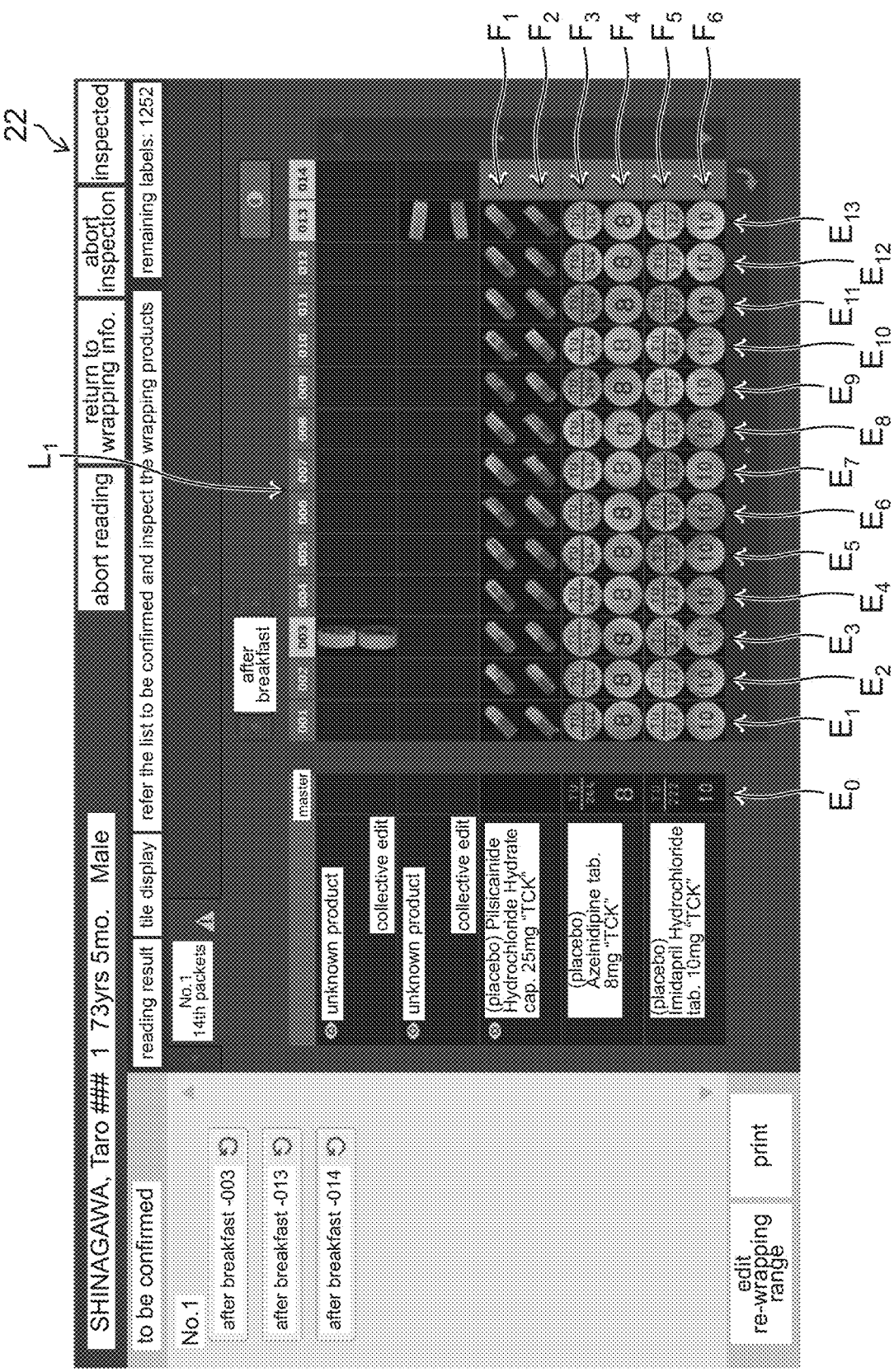
FIG. 32 shows a list table.

FIG. 32 shows the list table $L_1$ displayed on the display unit 22. Here, an example is shown where a drug A, a drug B and a drug C are packed in each of thirteen individual bags. The list table $L_1$ includes a column $E_0$ displaying the display images of the master images of the drugs to be dispensed, and columns $E_1$ to $E_{13}$ displaying the display images of the drugs packed in each individual bag.

Each of columns $E_0$ to $E_{13}$ is divided into a row $F_1$ displaying the display image on the front side of the drug A, a row $F_2$ displaying the display image on the rear side of the drug A, a row $F_3$ displaying the display image on the front side of the drug B, a row $F_4$ displaying the display image on the rear side of the drug B, a row $F_5$ displaying the display image on the front side of the drug C, and a row $F_6$ displaying the display image on the rear side of the drug C.

On each of the rows $F_1$ to $F_6$ on each of the columns $E_0$ to $E_{13}$, the display image corresponding to each position is displayed. The display image of the drug and the display image of the master image, which are displayed here, are aligned by the rotating unit 56 such that the engraved mark portions or the printed character portions are oriented in the same direction.

As shown in FIG. 32, the list table is displayed where the master image of the drug to be dispensed and the drug area image of each drug are positionally aligned and the engraved mark portion and the printed character portion are enhanced. Accordingly, it is possible to display them in a manner easily recognizable by the user. Note that the engraved mark portion and the printed character portion are enhanced here. Alternatively, a list table where one of the engraved mark portion and the printed character portion is enhanced may be displayed. Both the cases are encompassed by the concept of the list table where the engraved mark portion or the printed character portion is enhanced.

Figure 33:
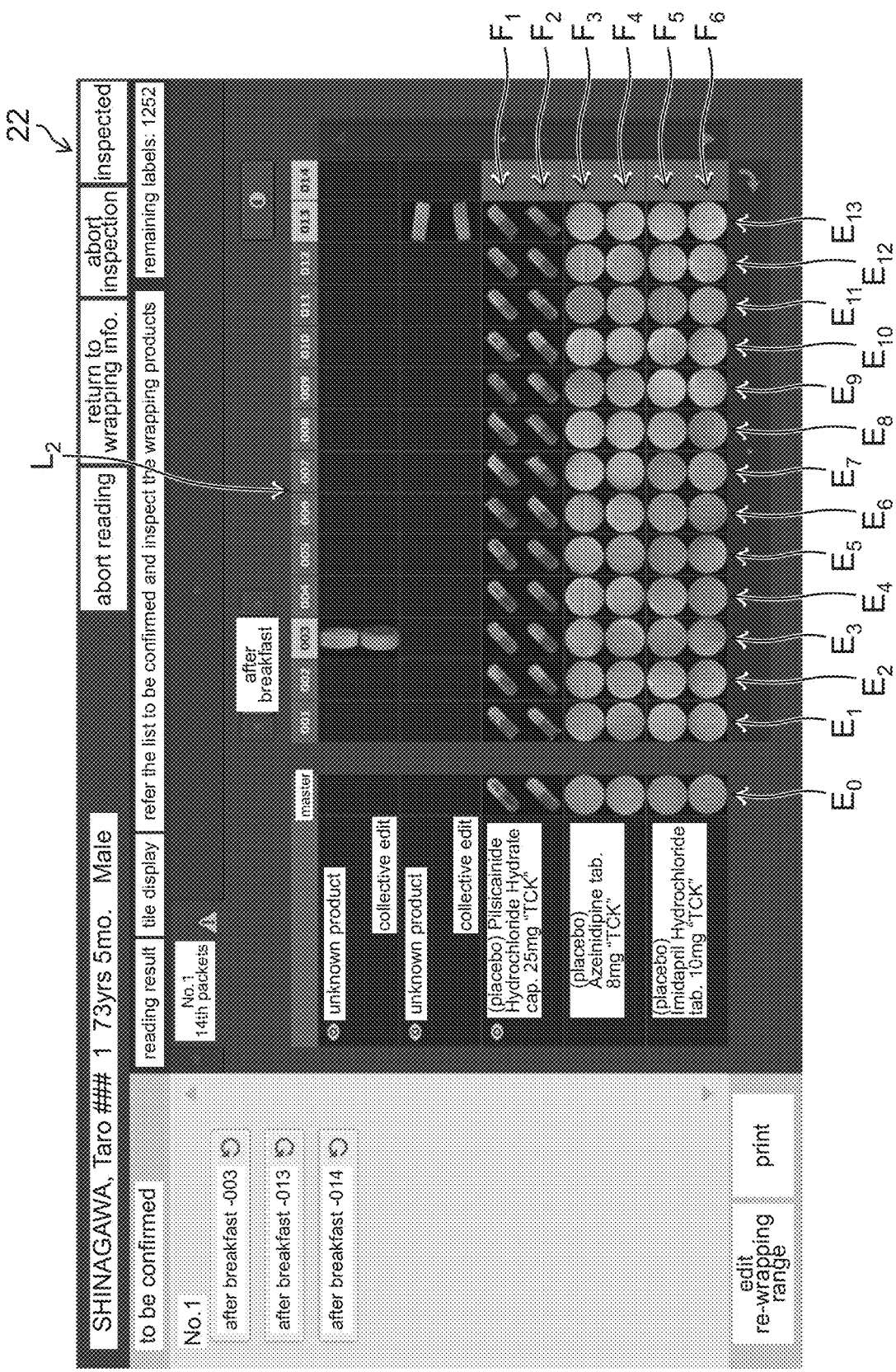
FIG. 33 shows a list table of a comparative example.

FIG. 33 shows a list table $L_2$ of a comparative example. The list table $L_2$ shown in FIG. 33 displays the master images and the drug area images without enhancement of the engraved mark portion and the printed character portion. The drug area images are viewed in a different manner depending on the positional relationship between the light source and the engraved mark portion. Here, the list table $L_2$ has a poor viewability.

In this embodiment, the difference image obtained by subtracting the drug area image from the composite image is used as the display image with the engraved mark portion of the drug being enhanced. However, the display image displayed in the list table is not limited to the difference image as long as a method can improve user's viewability for the engraved mark portion of the drug.

In this embodiment, the example where the drugs packed in the individual bags are inspected is described. Alternatively, the drug inspection assistance device 11 can inspect a drug placed on a Petri dish or a drug directly placed on a stage. However, inspection of the drugs packed in the individual bags is useful and preferable in view of operability.

Note that the drug inspection includes audit and differentiation (identification). In this embodiment, the example of supporting audit of drugs dispensed based on the prescription data is described. Alternatively, the drug inspection assistance device 11 is applicable to supporting drug differentiation. The drug differentiation is to identify the drug from the appearance of the drug. The drug discrimination can determine drugs carried by a hospitalized patient, for example.

<Other>

The image processing method described above can be configured as a program of causing a computer to achieve the obtaining function, the edge image generating function, the image composing function, the image comparing function, and the determining function. In addition, the image processing method can be configured as a non-transitory recording medium, such as a CD-ROM (Compact Disk-Read Only Memory), storing the program.

In the thus described embodiments, for example, the hardware structure of the processing unit that executes various kinds of processes, such as of the imaging control unit 128, the image comparing unit 130, the image processing unit 132, the correlation degree detecting unit 134, the determining unit 136, the edge image generating unit 182, and the image composing unit 184, is any of various processors as described below. The various processors include: a CPU (Central Processing Unit), which is a general-purpose processor executing software (program) to function as various processing units; a programmable logic device (PLD), such as an FPGA (Field Programmable Gate Array), which is a processor whose circuit configuration can be changed after production; and circuitry, such as an ASIC (Application Specific Integrated Circuit), which has a circuit configuration designed in a dedicated manner to execute a specific process.

One processing unit may include one among these various processors, or include the same kind or different kinds of two or more processors (e.g., multiple FPGAs or a combination of a CPU and an FPGA). Alternatively, multiple processing units may be made up of a single processor. Examples where multiple processing units are made up of a single processor include, firstly, a mode where as typified by a computer, such as a server and a client, a combination of one or more CPUs and software constitutes a single processor, and the processor functions as multiple processing units. Secondly, as typified by a system on chip (SoC), the examples include a mode of using a processor where the function of the entire system including multiple processing units is achieved by a single IC (Integrated Circuit) chip. As described above, various processing units are configured using one or more various processors as a hardware configuration.

Furthermore, more specifically, each of the hardware structures of these various processors is circuitry including combined circuit elements, such as semiconductor elements.

The technical scope of the present invention is not limited to the scope described in the above embodiments. The configurations and the like in the respective embodiments can be appropriately combined between the embodiments in a range without departing from the spirit of the present invention.

REFERENCE SIGNS LIST

10 Drug identification device
11 Drug inspection assistance device
12 Illuminating unit
14 Imaging unit
16 Prescription information obtaining unit
18 Storage unit
20 Processing unit
22 Display unit
24 Operation unit
32 Illumination control unit
34 Imaging control unit
35 Drug position obtaining unit
36 Master image generating unit
42 Collating unit
44 Update determining unit
46 Registering unit
48 Display control unit
49 Correlation value calculating unit
50 Reference position setting unit
52 List creating unit
54 Display image generating unit
56 Rotating unit
100 Drug identification device
102 Stage
102A Mounting surface
102B Rear surface
104 First light source
106 Second light source
108 Third light source
110 Fourth light source
112 Fifth light source
114 Sixth light source
116 Seventh light source
118 Eighth light source
120 Camera
122 Camera
124 Obtaining unit
126 Irradiating unit
128 Imaging control unit
130 Image comparing unit
132 Image processing unit
134 Correlation degree detecting unit
136 Determining unit
140 Drug identification device
142 Mounting-surface-side dome lamp 144 Light source supporting unit
144A Opening window
146 Point light source
148 Rear-surface-side dome lamp
150 Light source supporting unit
150A Opening window
152 Point light source
160 Drug identification device
162 First epi-illumination lamp
164 Light source
166 Half mirror
168 Second epi-illumination lamp
170 Light source
172 Half mirror
180 Drug identification device
182 Edge image generating unit
184 Image composing unit
$E_0$ to $E_{13}$ Column
$F_1$ to $F_6$ Row
$F_D$ Sobel filter
$F_{DL}$ Sobel filter
$F_{DR}$ Sobel filter
$F_L$ Sobel filter
$F_R$ Sobel filter
$F_U$ Sobel filter
$F_{UL}$ Sobel filter
$F_{UR}$ Sobel filter
$G_{A1}$ Omnidirectional incident image
$G_{A2}$ Omnidirectional corrected image
$G_{A3}$ Omnidirectional corrected image
$G_C$ Composite image
$G_{D1}$ Lower incident image
$G_{D11}$ Lower incident image
$G_{D12}$ Lower incident image
$G_{D13}$ Lower directional edge image
$G_{D2}$ Lower corrected image
$G_{D3}$ Lower corrected image
$G_{L1}$ Left incident image
$G_{L11}$ Left incident image
$G_{L12}$ Left incident image
$G_{L13}$ Left directional edge image
$G_{L2}$ Left corrected image
$G_{L3}$ Left corrected image
$G_{R1}$ Right incident image
$G_{R11}$ Right incident image
$G_{R12}$ Right incident image
$G_{R13}$ Right directional edge image
$G_{R2}$ Right corrected image
$G_{R3}$ Right corrected image
$G_{U1}$ Upper incident image
$G_{U11}$ Upper incident image
$G_{U12}$ Upper incident image
$G_{U13}$ Upper directional edge image
$G_{U2}$ Upper corrected image
$G_{U3}$ Upper corrected image
I Identification information
$L_1$ List table
$L_2$ List table
$L_L$ Illumination light
$L_R$ Illumination light
P Printed character
PB Strip package
$P_{CA}$ Profile
$P_{EAL}$ Profile
$P_{EAR}$ Profile
$P_{EBL}$ Profile
$P_{EBR}$ Profile
$P_{PAL}$ Profile
$P_{PAR}$ Profile
$P_{PAW}$ Profile
$P_{PBL}$ Profile
$P_{PBR}$ Profile
$P_{PBW}$ Profile
S Engraved mark
$S_L$ Surface
$S_R$ Surface
T Tablet
TP Package
S2 to S26 Steps of processes of drug identification method

What is claimed is:

1. An image processing device, comprising:
an obtaining unit configured to obtain a plurality of images of a drug having an engraved mark on a surface of the drug, with emitting directions of light to the surface different from each other;
an edge image generating unit configured to apply respectively to the plurality of images, edge extracting filters in directions in conformity with the emitting directions, the edge extracting filters having a larger size than half a width of a groove of the engraved mark, and generate a plurality of edge images; and
an image composing unit configured to compose the plurality of edge images and generate a composite image.

2. The image processing device according to claim 1, wherein the directions in conformity with the emitting directions include a direction of an emitting direction in plan view of the surface.

3. The image processing device according to claim 2, wherein the directions in conformity with the emitting directions include a direction inclined by 45 degrees from the direction of the emitting direction in plan view of the surface, and a direction inclined by −45 degrees from the direction of the emitting direction in plan view of the surface.

4. The image processing device according to claim 3, wherein the obtaining unit obtains four images of the drug, with the emitting directions of light to the surface being a first direction, a second direction, a third direction and a fourth direction, and
the second direction is a direction opposite to the first direction in plan view of the surface, the third direction is a direction orthogonal to the first direction in plan view of the surface, and the fourth direction is a direction opposite to the third direction in plan view of the surface.

5. A drug identification device, comprising:
a stage configured to place a drug thereon, the drug having an engraved mark on a surface of the drug;
an irradiating unit configured to include a plurality of light sources with emitting directions of light to the surface different from each other;
an imaging unit configured to obtain a plurality of images taken by imaging the drug with the surface irradiated with light by the light sources;
an edge image generating unit configured to apply respectively to the plurality of images, edge extracting filters in directions in conformity with the emitting directions, the edge extracting filters having a larger size than half a width of a groove of the engraved mark, and generate a plurality of edge images; and
an image composing unit configured to compose the plurality of edge images and generate a composite image.

6. A drug identification device comprising:
a stage configured to place a drug thereon, the drug having an engraved mark on a surface of the drug;
an irradiating unit configured to include a plurality of light sources with emitting directions of light to the surface different from each other;
an imaging unit configured to obtain a plurality of images taken by imaging the drug with the surface irradiated with light by the light sources;
an edge image generating unit configured to apply respectively to the plurality of images, edge extracting filters in directions in conformity with the emitting directions, the edge extracting filters having a size in conformity with a width of a groove of the engraved mark, and generate a plurality of edge images; and
an image composing unit configured to compose the plurality of edge images and generate a composite image,
wherein the irradiating unit comprises a first light source configured to emit light in a first direction, a second light source configured to emit light in a second direction, a third light source configured to emit light in a third direction, and a fourth light source configured to emit light in a fourth direction, and
the second direction is a direction opposite to the first direction in plan view of the surface, the third direction is a direction orthogonal to the first direction in plan view of the surface, and the fourth direction is a direction opposite to the third direction in plan view of the surface.

7. The drug identification device according to claim 6, wherein the irradiating unit comprises a fifth light source configured to emit light in a fifth direction, a sixth light source configured to emit light in a sixth direction, a seventh light source configured to emit light in a seventh direction, and an eighth light source configured to emit light in an eighth direction,
the sixth direction is a direction opposite to the fifth direction in plan view of the surface, the seventh direction is a direction orthogonal to the fifth direction in plan view of the surface and the eighth direction is a direction opposite to the seventh direction in plan view of the surface,
the stage is made of a material having a light transparency,
the first light source, the second light source, the third light source and the fourth light source are disposed on one surface side of the stage, and
the fifth light source, the sixth light source, the seventh light source and the eighth light source are disposed on another surface side of the stage, the another surface side being different from the one surface side.

8. The drug identification device according to claim 6, wherein the edge image generating unit applies the edge extracting filters having a larger size than half the width of the groove of the engraved mark, to generate the plurality of edge images.

9. An image processing method, comprising:
an obtaining step of obtaining a plurality of images of a drug having an engraved mark on a surface of the drug, with emitting directions of light to the surface different from each other;
an edge image generating step of applying respectively to the plurality of images, edge extracting filters in directions in conformity with the emitting directions, the edge extracting filters having a larger size than half a width of a groove of the engraved mark, to generate a plurality of edge images; and
an image composing step of composing the plurality of edge images to generate a composite image.

10. A non-transitory computer-readable recording medium wherein when an instruction stored in the recording medium is read by a computer, the instruction causes the computer to execute:
an obtaining function of obtaining a plurality of images of a drug having an engraved mark on a surface of the drug, with emitting directions of light to the surface different from each other;
an edge image generating function of respectively applying to the plurality of images, edge extracting filters in directions in conformity with the emitting directions, the edge extracting filters having a larger size than half a width of a groove of the engraved mark, to generate a plurality of edge images; and
an image composing function of composing the plurality of edge images to generate a composite image.

11. An drug inspection assistance device which inspects a drug, comprising:
an obtaining unit configured to obtain a plurality of images of a drug having an engraved mark on a surface of the drug, with emitting directions of light to the surface different from each other;
an edge image generating unit configured to apply respectively to the plurality of images, edge extracting filters in directions in conformity with the emitting directions, the edge extracting filters having a larger size than half a width of a groove of the engraved mark, and generate a plurality of edge images;
an image composing unit configured to compose the plurality of edge images and generate a composite image;
a display image generating unit configured to generate, as a display image where the engraved mark is enhanced, a difference image obtained by subtracting, from the composite image, a drug area image corresponding to the composite image;
a drug discriminating unit configured to collate drug master images of drugs from a drug database including drug master images, with taken images obtained by imaging drugs to be inspected, and discriminate which drugs the drugs present in the taken images are; and
a list creating unit configured to create a list table of the drugs to be inspected, the list table representing drug master images of the drugs and the difference image, with positions of the drug master images being aligned to positions of the difference image, and engraved mark portions or printed character portions being enhanced.

12. An image processing device, comprising:
an obtaining unit configured to obtain a plurality of images of a drug having an engraved mark on a surface of the drug, with emitting directions of light to the surface different from each other;
an edge image generating unit configured to apply respectively to the plurality of images, edge extracting filters in directions in conformity with the emitting directions, the edge extracting filters having a size in conformity with a width of a groove of the engraved mark, and generate a plurality of edge images; and
an image composing unit configured to compose the plurality of edge images and generate a composite image,
wherein the directions in conformity with the emitting directions include a direction of an emitting direction in plan view of the surface, and further include a direction inclined by 45 degrees from the direction of the emitting direction in plan view of the surface, and a direction inclined by −45 degrees from the direction of the emitting direction in plan view of the surface.

13. An image processing device, comprising an obtaining unit configured to obtain a plurality of images of a drug having an engraved mark on a surface of the drug, with emitting directions of light to the surface different from each other;

an edge image generating unit configured to apply respectively to the plurality of images, edge extracting filters in directions in conformity with the emitting directions, the edge extracting filters having a size in conformity with a width of a groove of the engraved mark, and generate a plurality of edge images; and an image composing unit configured to compose the plurality of edge images and generate a composite image, wherein the obtaining unit obtains four images of the drug, with the emitting directions of light to the surface being a first direction, a second direction, a third direction and a fourth direction, and the second direction is a direction opposite to the first direction in plan view of the surface, the third direction is a direction orthogonal to the first direction in plan view of the surface, and the fourth direction is a direction opposite to the third direction in plan view of the surface.

14. The image processing device according to claim 13, wherein the edge image generating unit applies the edge extracting filters having a larger size than half the width of the groove of the engraved mark, to generate the plurality of edge images.

* * * * *